US012115414B1

(12) United States Patent
Chuang

(10) Patent No.: US 12,115,414 B1
(45) Date of Patent: Oct. 15, 2024

(54) ATHLETIC PERFORMANCE AND TECHNIQUE MONITORING

(71) Applicant: Thomas C. Chuang, Menlo Park, CA (US)

(72) Inventor: Thomas C. Chuang, Menlo Park, CA (US)

(*) Notice: Subject to any disclaimer, the term of this patent is extended or adjusted under 35 U.S.C. 154(b) by 0 days.

(21) Appl. No.: 17/985,358

(22) Filed: Nov. 11, 2022

Related U.S. Application Data

(63) Continuation of application No. 17/033,421, filed on Sep. 25, 2020, now Pat. No. 11,511,154, which is a
(Continued)

(51) Int. Cl.
*A63B 24/00* (2006.01)
*A61B 5/00* (2006.01)
(Continued)

(52) U.S. Cl.
CPC .......... *A63B 24/0006* (2013.01); *A61B 5/112* (2013.01); *A61B 5/681* (2013.01);
(Continued)

(58) Field of Classification Search
CPC . A63B 24/00; A63B 24/0003; A63B 24/0006; A63B 24/0021; A63B 1/00; A63B 69/00; A63B 69/0028; A63B 71/0619; A63B 2220/12; A63B 2220/16; A63B 2220/20; A63B 2220/22; A63B 2220/40; A63B 2220/833; A63B 2220/836; A63B 2230/06; A63B 2203/18; G06T 7/11; G06T 7/12; G06T 2207/10056; G06T 2207/30024; G16H 50/30; G06V 20/698; G06V 40/23; G06F 18/2193; A61B 5/0002; A61B 5/112; A61B 5/681; A61B 5/1112; A61B 2560/0242; G01N 33/57415; G01N 2800/52; G01N 2800/54; G01P 3/00; G01P 13/00; G01S 19/19; G01S 19/52
See application file for complete search history.

(56) References Cited

U.S. PATENT DOCUMENTS 4,458,802 A 7/1984 MacIver
4,528,643 A 7/1985 Freeny, Jr.
(Continued)

FOREIGN PATENT DOCUMENTS

EP 1066793 1/2001
EP 2363178 A2 9/2011
(Continued)

OTHER PUBLICATIONS

R. J. Beck, Changes in the Gait Patterns of Growing Children, Journal of Bone and Joint Surgery, 1981, pp. 1452-1457, USA.
(Continued)

*Primary Examiner* — Timothy A Musselman
(74) *Attorney, Agent, or Firm* — Chuang Intellectual Property Law; Thomas Chuang

(57) ABSTRACT

Methods and apparatuses for athletic performance and technique monitoring are disclosed. In one example, a sensor output is received associated with a movement of a user torso during a running motion. The sensor output is analyzed to identify an undesirable torso motion.

29 Claims, 8 Drawing Sheets

Related U.S. Application Data continuation of application No. 16/207,105, filed on Dec. 1, 2018, now Pat. No. 10,789,708, which is a continuation of application No. 15/613,114, filed on Jun. 2, 2017, now Pat. No. 10,143,887, which is a continuation of application No. 15/375,524, filed on Dec. 12, 2016, now Pat. No. 9,669,259, which is a continuation of application No. 13/487,024, filed on Jun. 1, 2012, now Pat. No. 9,533,182, which is a continuation of application No. 13/422,878, filed on Mar. 16, 2012, now Pat. No. 8,573,982.

(60) Provisional application No. 61/453,960, filed on Mar. 18, 2011.

(51) Int. Cl.
| | | |
|---|---|---|
| *A61B 5/11* | (2006.01) | |
| *A63B 1/00* | (2006.01) | |
| *A63B 69/00* | (2006.01) | |
| *A63B 71/06* | (2006.01) | |
| *G01N 33/574* | (2006.01) | |
| *G01P 3/00* | (2006.01) | |
| *G01P 13/00* | (2006.01) | |
| *G01S 19/19* | (2010.01) | |
| *G01S 19/52* | (2010.01) | |
| *G06F 18/21* | (2023.01) | |
| *G06T 7/00* | (2017.01) | |
| *G06T 7/12* | (2017.01) | |
| *G06V 20/69* | (2022.01) | |
| *G06V 40/20* | (2022.01) | |
| *G09B 19/00* | (2006.01) | |
| *G16H 50/30* | (2018.01) | |
| *G06T 7/11* | (2017.01) | |

(52) U.S. Cl.
CPC ............ *A63B 1/00* (2013.01); *A63B 24/0003* (2013.01); *A63B 24/0021* (2013.01); *A63B 69/0028* (2013.01); *A63B 71/0619* (2013.01); *G01N 33/57415* (2013.01); *G01P 3/00* (2013.01); *G01P 13/00* (2013.01); *G01S 19/19* (2013.01); *G01S 19/52* (2013.01); *G06F 18/2193* (2023.01); *G06T 7/0012* (2013.01); *G06T 7/12* (2017.01); *G06V 20/698* (2022.01); *G06V 40/23* (2022.01); *G09B 19/00* (2013.01); *G09B 19/0038* (2013.01); *G16H 50/30* (2018.01); *A61B 5/0002* (2013.01); *A61B 5/1112* (2013.01); *A61B 2560/0242* (2013.01); *A63B 24/00* (2013.01); *A63B 2220/12* (2013.01); *A63B 2220/16* (2013.01); *A63B 2220/20* (2013.01); *A63B 2220/22* (2013.01); *A63B 2220/40* (2013.01); *A63B 2220/833* (2013.01); *A63B 2220/836* (2013.01); *A63B 2230/06* (2013.01); *A63C 2203/18* (2013.01); *G01N 2800/52* (2013.01); *G01N 2800/54* (2013.01); *G06T 7/11* (2017.01); *G06T 2207/10056* (2013.01); *G06T 2207/30024* (2013.01)

(56) References Cited

U.S. PATENT DOCUMENTS

| | | |
|---|---|---|
| 4,703,445 A | 10/1987 | Dassler |
| 4,736,312 A | 4/1988 | Dassler |
| 4,763,287 A | 8/1988 | Gerhaeuser |
| 4,866,661 A | 9/1989 | De Prins |
| 4,886,661 A | 12/1989 | Cyprien Guy |
| 5,028,866 A | 7/1991 | Wiese |
| 5,088,586 A | 2/1992 | Isobe |
| 5,095,195 A | 3/1992 | Harman |
| 5,130,792 A | 7/1992 | Tindell |
| 5,143,193 A | 9/1992 | Geraci |
| 5,247,347 A | 9/1993 | Litteral |
| 5,445,295 A | 8/1995 | Brown |
| 5,471,405 A | 11/1995 | Marsh |
| 5,523,551 A | 6/1996 | Scott |
| 5,586,398 A | 12/1996 | Carlson |
| 5,633,839 A | 5/1997 | Alexander |
| 5,664,110 A | 9/1997 | Green et al. |
| 5,664,210 A | 9/1997 | Fleming |
| 5,678,448 A | 10/1997 | Fullen |
| 5,684,110 A | 11/1997 | Kawamura |
| 5,689,099 A | 11/1997 | Domburg |
| 5,704,017 A | 12/1997 | Heckerman |
| 5,790,426 A | 8/1998 | Robinson |
| 5,794,217 A | 8/1998 | Allen |
| 5,842,199 A | 11/1998 | Miller |
| 5,867,799 A | 2/1999 | Lang |
| 5,884,282 A | 3/1999 | Robinson |
| 5,899,963 A | 5/1999 | Hutchings |
| 5,918,014 A | 6/1999 | Robinson |
| 5,918,213 A | 6/1999 | Bernard |
| 5,983,214 A | 11/1999 | Lang |
| 6,011,772 A | 1/2000 | Rollhaus |
| 6,012,052 A | 1/2000 | Altschuler |
| 6,013,007 A | 1/2000 | Root |
| 6,016,475 A | 1/2000 | Miller |
| 6,018,705 A | 1/2000 | Gaudet |
| 6,029,161 A | 2/2000 | Lang |
| 6,029,195 A | 2/2000 | Herz |
| 6,032,530 A | 3/2000 | Hock |
| 6,041,311 A | 3/2000 | Chislenko |
| 6,049,777 A | 4/2000 | Sheena |
| 6,055,314 A | 4/2000 | Spies |
| 6,092,049 A | 7/2000 | Chislenko |
| 6,108,493 A | 8/2000 | Miller |
| 6,112,186 A | 8/2000 | Bergh |
| 6,119,101 A | 9/2000 | Peckover |
| 6,145,389 A | 11/2000 | Ebeling |
| 6,175,608 B1 | 1/2001 | Pyles |
| 6,236,985 B1 | 5/2001 | Aggarwal |
| 6,286,139 B1 | 9/2001 | Decinque |
| 6,292,792 B1 | 9/2001 | Baffes |
| 6,301,964 B1 | 10/2001 | Fyfe |
| 6,308,168 B1 | 10/2001 | Dovich |
| 6,321,179 B1 | 11/2001 | Glance |
| 6,321,221 B1 | 11/2001 | Bieganski |
| 6,330,490 B1 | 12/2001 | Kim |
| 6,330,592 B1 | 12/2001 | Makuch |
| 6,334,127 B1 | 12/2001 | Bieganski |
| 6,338,933 B1 | 1/2002 | Lawandy |
| 6,343,063 B1 | 1/2002 | Rollhaus |
| 6,356,856 B1 | 3/2002 | Damen |
| 6,389,372 B1 | 5/2002 | Glance |
| 6,412,012 B1 | 6/2002 | Bieganski |
| 6,418,421 B1 | 7/2002 | Hurtado |
| 6,460,076 B1 | 10/2002 | Srinivasan |
| 6,484,123 B2 | 11/2002 | Srivastava |
| 6,487,539 B1 | 11/2002 | Aggarwal |
| 6,487,541 B1 | 11/2002 | Aggarwal |
| 6,493,652 B1 | 12/2002 | Ohlenbusch |
| 6,496,816 B1 | 12/2002 | Thiesson |
| 6,513,532 B2 | 2/2003 | Mault |
| 6,571,150 B2 | 5/2003 | Arai |
| 6,584,450 B1 | 6/2003 | Hastings |
| 6,606,744 B1 | 8/2003 | Mikurak |
| 6,611,789 B1 | 8/2003 | Darley |
| 6,611,812 B2 | 8/2003 | Hurtado |
| 6,655,580 B1 | 12/2003 | Ergo |
| 6,714,643 B1 | 3/2004 | Gargeya |
| 6,738,726 B2 | 5/2004 | Guzman |
| 6,836,744 B1 | 12/2004 | Asphahani |
| 6,845,361 B1 | 1/2005 | Dowling |
| 6,876,947 B1 | 4/2005 | Darley |
| 6,882,955 B1 | 4/2005 | Ohlenbusch |
| 6,898,550 B1 | 5/2005 | Blackadar |
| 6,997,882 B1 | 2/2006 | Parker |

(56) References Cited

U.S. PATENT DOCUMENTS

| | | | |
|---|---|---|---|
| 7,028,547 B2 | 4/2006 | Shiratori | |
| 7,085,727 B2 | 8/2006 | Vanorman | |
| 7,099,846 B1 | 8/2006 | Ishibashi | |
| 7,174,362 B1 | 2/2007 | Lee | |
| 7,220,220 B2 | 5/2007 | Stubbs | |
| 7,237,446 B2 | 7/2007 | Chan | |
| 7,254,516 B2 | 8/2007 | Case, Jr. | |
| 7,355,519 B2 | 4/2008 | Grold | |
| 7,383,728 B2 | 6/2008 | Noble | |
| 7,403,910 B1 | 7/2008 | Hastings | |
| 7,457,724 B2 | 11/2008 | Vock | |
| 7,467,060 B2 | 12/2008 | Kulach | |
| 7,579,946 B2 | 8/2009 | Case, Jr. | |
| 7,596,891 B2 | 10/2009 | Carnes | |
| 7,602,301 B1 | 10/2009 | Stirling | |
| 7,603,255 B2 | 10/2009 | Case, Jr. | |
| 7,607,243 B2 | 10/2009 | Berner, Jr. | |
| 7,617,071 B2 | 11/2009 | Darley | |
| 7,647,196 B2 | 1/2010 | Kahn | |
| 7,648,441 B2 | 1/2010 | Silk | |
| 7,653,508 B1 | 1/2010 | Kahn | |
| 7,771,320 B2 | 8/2010 | Riley | |
| 7,801,643 B2 | 9/2010 | Takenaka | |
| 7,827,000 B2 | 11/2010 | Stirling | |
| 7,857,772 B2 | 12/2010 | Bouvier | |
| 7,901,325 B2 | 3/2011 | Henderson | |
| 7,912,672 B2 | 3/2011 | Feichtinger | |
| 7,980,999 B2 | 7/2011 | Kawaguchi | |
| 8,015,732 B2 | 9/2011 | Berner | |
| 8,028,443 B2 | 10/2011 | Case | |
| 8,033,959 B2 | 10/2011 | Oleson | |
| 8,055,469 B2 | 11/2011 | Kulach | |
| 8,056,268 B2 | 11/2011 | Dibenedetto | |
| 8,060,337 B2 | 11/2011 | Kulach | |
| 8,070,654 B2 | 12/2011 | Chapa, Jr. | |
| 8,112,251 B2 | 2/2012 | Case | |
| 8,128,410 B2 | 3/2012 | Prstojevich | |
| 8,172,722 B2 * | 5/2012 | Molyneux | A63B 24/0021 482/901 |
| 8,253,586 B1 | 8/2012 | Matak | |
| 8,337,212 B2 | 12/2012 | Prstojevich | |
| 8,460,001 B1 | 6/2013 | Chuang | |
| 8,480,541 B1 | 7/2013 | Brunts | |
| 8,573,982 B1 | 11/2013 | Chuang | |
| 8,584,450 B2 | 11/2013 | Alizon | |
| 8,702,430 B2 | 4/2014 | Dibenedetto | |
| 8,784,274 B1 | 7/2014 | Chuang | |
| 9,223,936 B2 | 12/2015 | Aragones | |
| 9,314,192 B2 | 4/2016 | Goris | |
| 9,665,873 B2 | 5/2017 | Ackland | |
| 2001/0012483 A1 | 8/2001 | Kono | |
| 2001/0013120 A1 | 8/2001 | Tsukamoto | |
| 2001/0020236 A1 | 9/2001 | Cannon | |
| 2001/0022828 A1 | 9/2001 | Pyles | |
| 2001/0025269 A1 | 9/2001 | Otsuka | |
| 2001/0035903 A1 | 11/2001 | Trane | |
| 2001/0036271 A1 | 11/2001 | Javed | |
| 2002/0019296 A1 | 2/2002 | Freeman | |
| 2002/0032905 A1 | 3/2002 | Sherr | |
| 2002/0040601 A1 | 4/2002 | Fyfe | |
| 2002/0046085 A1 | 4/2002 | Rochon | |
| 2002/0049679 A1 | 4/2002 | Russell | |
| 2002/0062274 A1 | 5/2002 | Tamayama | |
| 2002/0069138 A1 | 6/2002 | Horibe | |
| 2002/0073033 A1 | 6/2002 | Sherr | |
| 2002/0074398 A1 | 6/2002 | Lancos | |
| 2002/0099516 A1 | 7/2002 | Guzman | |
| 2002/0114465 A1 | 8/2002 | Shen-Orr | |
| 2002/0138379 A1 | 9/2002 | Yuasa | |
| 2002/0154157 A1 | 10/2002 | Sherr | |
| 2002/0162112 A1 | 10/2002 | Javed | |
| 2003/0040962 A1 | 2/2003 | Lewis | |
| 2003/0056212 A1 | 3/2003 | Siegel | |
| 2003/0069854 A1 | 4/2003 | Hsu | |
| 2003/0115069 A1 | 6/2003 | Pence | |
| 2003/0135467 A1 | 7/2003 | Okamoto | |
| 2003/0155417 A1 | 8/2003 | Fairman | |
| 2003/0172035 A1 | 9/2003 | Cronce | |
| 2004/0068451 A1 | 4/2004 | Lenk | |
| 2004/0077975 A1 | 4/2004 | Zimmerman | |
| 2004/0102931 A1 | 5/2004 | Ellis | |
| 2004/0103092 A1 | 5/2004 | Tuzhilin | |
| 2004/0122483 A1 | 6/2004 | Nathan | |
| 2004/0128250 A1 | 7/2004 | Fox | |
| 2004/0158871 A1 | 8/2004 | Jacobson | |
| 2005/0021478 A1 | 1/2005 | Gautier | |
| 2005/0086127 A1 | 4/2005 | Hastings | |
| 2005/0125307 A1 | 6/2005 | Hunt | |
| 2005/0184878 A1 | 8/2005 | Grold | |
| 2005/0192871 A1 | 9/2005 | Galuten | |
| 2005/0193094 A1 | 9/2005 | Robbin | |
| 2006/0136173 A1 | 6/2006 | Case, Jr. | |
| 2006/0178918 A1 | 8/2006 | Mikurak | |
| 2006/0206386 A1 | 9/2006 | Walker | |
| 2006/0265187 A1 | 11/2006 | Vock | |
| 2007/0006489 A1 | 1/2007 | Case, Jr. | |
| 2007/0068244 A1 | 3/2007 | Billing | |
| 2007/0123806 A1 | 5/2007 | Bouvier | |
| 2007/0202478 A1 | 8/2007 | Al-Obaidi | |
| 2007/0203665 A1 | 8/2007 | Darley | |
| 2007/0208531 A1 | 9/2007 | Darley | |
| 2007/0208544 A1 | 9/2007 | Kulach | |
| 2007/0260421 A1 | 11/2007 | Berner | |
| 2007/0272011 A1 | 11/2007 | Chapa | |
| 2008/0046179 A1 | 2/2008 | Mackintosh | |
| 2008/0096726 A1 | 4/2008 | Riley | |
| 2008/0146968 A1 | 6/2008 | Hanawaka | |
| 2008/0190202 A1 | 8/2008 | Kulach | |
| 2008/0206726 A1 | 8/2008 | Kalisvaart | |
| 2008/0214360 A1 | 9/2008 | Stirling | |
| 2008/0218310 A1 | 9/2008 | Alten | |
| 2008/0249736 A1 | 10/2008 | Prstojevich | |
| 2008/0284650 A1 | 11/2008 | MacIntosh | |
| 2008/0294019 A1 | 11/2008 | Tran | |
| 2009/0043531 A1 | 2/2009 | Kahn | |
| 2009/0046056 A1 | 2/2009 | Rosenberg | |
| 2009/0047645 A1 | 2/2009 | Dibenedetto | |
| 2009/0076765 A1 | 3/2009 | Kulach | |
| 2009/0135001 A1 | 5/2009 | Yuk | |
| 2009/0190713 A1 | 7/2009 | Wai | |
| 2009/0233770 A1 | 9/2009 | Vincent | |
| 2010/0004097 A1 | 1/2010 | D Eredita | |
| 2010/0004860 A1 | 1/2010 | Chernoguz | |
| 2010/0042182 A1 | 2/2010 | Chan | |
| 2010/0059561 A1 | 3/2010 | Ellis | |
| 2010/0062740 A1 | 3/2010 | Ellis | |
| 2010/0063779 A1 | 3/2010 | Schrock | |
| 2010/0099539 A1 | 4/2010 | Haataja | |
| 2010/0156653 A1 | 6/2010 | Chaudhari | |
| 2010/0184564 A1 | 7/2010 | Molyneux | |
| 2010/0201512 A1 | 8/2010 | Stirling | |
| 2010/0204615 A1 | 8/2010 | Kyle | |
| 2010/0227738 A1 | 9/2010 | Henderson | |
| 2010/0228520 A1 | 9/2010 | Maxwell | |
| 2010/0260011 A1 | 10/2010 | Berger | |
| 2010/0292599 A1 | 11/2010 | Oleson | |
| 2010/0298660 A1 | 11/2010 | McCombie | |
| 2011/0003665 A1 | 1/2011 | Burton | |
| 2011/0022349 A1 | 1/2011 | Stirling | |
| 2011/0054809 A1 | 3/2011 | Templeman | |
| 2011/0092860 A1 | 4/2011 | Salarian | |
| 2011/0145162 A1 | 6/2011 | Vock | |
| 2011/0178759 A1 | 7/2011 | Uchida | |
| 2011/0184225 A1 | 7/2011 | Whitall | |
| 2011/0196264 A1 | 8/2011 | Asada | |
| 2011/0208444 A1 | 8/2011 | Solinsky | |
| 2011/0264401 A1 | 10/2011 | Niemimaeki | |
| 2012/0015779 A1 | 1/2012 | Powch | |
| 2012/0035509 A1 | 2/2012 | Wilson | |
| 2012/0123569 A1 | 5/2012 | Prstojevich | |
| 2012/0183939 A1 * | 7/2012 | Aragones | A63B 24/0062 434/247 |
| 2012/0183940 A1 | 7/2012 | Aragones | |
| 2012/0239333 A1 | 9/2012 | Keene | |

(56) References Cited

U.S. PATENT DOCUMENTS

| | | |
|---|---|---|
| 2012/0271143 A1 | 10/2012 | Aragones |
| 2013/0053990 A1 | 2/2013 | Ackland |
| 2013/0103170 A1 | 4/2013 | Prstojevich |
| 2013/0211775 A1 | 8/2013 | Statham |
| 2014/0315690 A1 | 10/2014 | Corbalis |

FOREIGN PATENT DOCUMENTS

| | | |
|---|---|---|
| WO | 2007017739 | 2/2007 |
| WO | WO2007017739 A3 | 2/2007 |
| WO | WO2007082389 A1 | 7/2007 |
| WO | WO2010129252 A1 | 11/2010 |
| WO | WO2010126825 A1 | 1/2011 |

OTHER PUBLICATIONS

K. Berg, Endurance Training and Performance in Runners: Research Limitations Unanswered Questions, Sports Medicine, Feb. 2003, pp. 59-73, 33(1):59-73, Adis International Limited, United Kindom.

J. Brisswalter, et al., Consequences of Drafting on Human Locomotion: Benefits on Sports Performance, International Journal of Sports Physiology and Performance, 2008, pp. 3-15, Human Kinetics, USA.

G. Cappellini, et al., Motor Patterns in Human Walking and Running, J Neurophysiol, 2006, pp. 3426-3437, 95: 3426-3437, American Physiological Society, USA.

G. Cavagna et al., Mechanical work in running, J. Appl. Physiol., 1964, pp. 249-256, 19(2): 249-256, American Physiological Society, United States.

M. Gardner, et al., Partial Body Weight Support With Treadmill Locomotion to Improve Gait After Incomplete Spinal Cord Injury: A Single-Subject Experimental Design, Physical Therapy, Apr. 1998, pp. 361-374, vol. 78, No. 4, USA.

H. Kunz et al., Biomechanical analysis of Sprinting: Decathletes versus Champions, Brit. J. Sports Med., Sep. 1981, pp. 177-181, vol. 15, No. 3, BMJ Group, United Kingdom.

J. Mercer, et al., The Physiological Importance of Preffered Stride Frequency During Running at Different Speeds, Journal of Exercise Physiology, Jun. 2008, pp. 26-32, vol. 11, No. 3, ASEP, USA.

G. Millet, Physiological and biomechanical adaptations to the cycle to run transition in Olympic triathlon: review and practical recommendations for training, British Journal of Sports Medicine, 2000, pp. 384-390, 34: 384-390, United Kingdom.

A. Patla, Understanding the Roles of Vision in the Control of Human Locomotion, Gait & Posture, 1997, pp. 54-69, Elsevier Science, Netherlands.

M Rodgers, Dynamic Foot Biomechanics, Journal of Orthopaedic and Sports Physical Therapy, Jun. 1995, pp. 306-316, vol. 21, No. 6, USA.

United States Patent and Trademark Office, "Communication" for U.S. Appl. No. 13/422,878, dated Feb. 1, 2013 (including patents and publications in List of References (PTO-892).

United States Patent and Trademark Office, "Notice of Allowance" for U.S. Appl. No. 13/375,524, dated Apr. 19, 2017 (including patents and publications in List of References (PTO-892).

United States Patent and Trademark Office, "Communication" for U.S. Appl. No. 13/487,024, dated Aug. 30, 2012 (including patents and publications in List of References (PTO-892).

United States Patent and Trademark Office, "Communication" for U.S. Appl. No. 13/422,484, dated May 1, 2013 (including patents and publications in List of References (PTO-892).

United States Patent and Trademark Office, "Communication" for U.S. Appl. No. 13/423,006, dated Sep. 11, 2013 (including patents and publications in List of References (PTO-892).

United States Patent and Trademark Office, "Communication" for U.S. Appl. No. 14/306,152, dated Aug. 11, 2016 (including patents and publications in List of References (PTO-892).

United States Patent and Trademark Office, "Communication" for copending U.S. Appl. No. 13/487,024.

United States Patent and Trademark Office, Communication for U.S. Appl. No. 13/613,114.

Anthropometric reference data for children and adults: United States, 1988-1994. National Center for Health Statistics. Vital Health Stat 11 (249). Apr. 2009.

Athlete's Acceleration, "Arm Action for Speed", accessed at: https://www.athletesacceleration.com/armaction1.html (2010) (https://web.archive.org/web/20100619005235/http://www.athletesacceleration.com:80/armaction1.html).

Bamberg et al. "Gait Analysis Using a Shoe-Integrated Wireless Sensor System" IEEE Transactions on Information Technology in Biomedicine, vol. 12, No. 4, Jul. 2008.

Chen, et al. "Intelligent Shoes for Abnormal Gait Detection". 2008 IEEE International Conference on Robotics and Automation Pasadena, CA, USA, May 19-23, 2008.

Morris Rick, "Overstriding and how to correct it" May 31, 2009.

Morris, et al. Shoe Integrated Sensor System for Wireless Gait Analysis and Real time feedback. Oct. 23-26, 2012.

United States Patent and Trademark Office, "Communication" for U.S. Appl. No. 13/754,901, dated Jul. 6, 2015.

\* cited by examiner

US 12,115,414 B1

ATHLETIC PERFORMANCE AND TECHNIQUE MONITORING

CROSS REFERENCE TO RELATED APPLICATIONS

This application is a Continuation Application of application Ser. No. 17/033,421 filed Dec. Sep. 25, 2020, which is a Continuation Application of application Ser. No. 16/207, 105 filed Dec. 1, 2018 (Issued as U.S. Pat. No. 10,789,708), which is a Continuation Application of application Ser. No. 15/613,114 filed Jun. 2, 2017 (Issued as U.S. Pat. No. 10,143,887), which is a Continuation Application of application Ser. No. 15/375,524 filed Dec. 12, 2016 (Issued as U.S. Pat. No. 9,669,259), which is a Continuation Application of application Ser. No. 13/487,024 filed Jun. 1, 2012 (Issued as U.S. Pat. No. 9,533,182), which is a Continuation Application of application Ser. No. 13/422,878 filed Mar. 16, 2012 (Issued as U.S. Pat. No. 8,573,982), which claims priority to Provisional Patent Application No. 61/453,960, to Thomas C. Chuang, and filed Mar. 18, 2011, the entire disclosures of which are incorporated herein by reference for all purposes.

This application is related to application Ser. No. 15/355, 412 filed Nov. 18, 2016 (Issued as U.S. Pat. No. 10,384, 098), which is a Continuation Application of application Ser. No. 13/487,024 filed Jun. 1, 2012 (Issued as U.S. Pat. No. 9,533,182), which is a Continuation Application of application Ser. No. 13/422,878 filed Mar. 16, 2012 (Issued as U.S. Pat. No. 8,573,982), which claims priority to Provisional Patent Application No. 61/453,960, to Thomas C. Chuang, and filed Mar. 18, 2011.

BACKGROUND OF THE INVENTION

Proper running form is essential for a runner to achieve his or her best results. In the prior art, various systems exist to monitor running parameters such as speed, distance, heart rate, and cadence. However, parameters such as these do not directly monitor the form or technique of a runner. As a result, methods and apparatuses for athletic performance monitoring associated with technique or form are needed.

BRIEF DESCRIPTION OF THE DRAWINGS

The present invention will be readily understood by the following detailed description in conjunction with the accompanying drawings, wherein like reference numerals designate like structural elements.

DESCRIPTION OF SPECIFIC EMBODIMENTS

Figure 1:
FIG. 1 illustrates a system for athletic performance monitoring being worn by a runner in one example.

Methods and apparatuses for athletic performance and technique monitoring are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that is known in the technical fields related to the invention have not been described in detail so as not to unnecessarily obscure the present invention.

Methods and apparatuses are described for determining proper arm swing during an athletic activity. Proper arm swing during running is important for several reasons. A proper arm swing, operating fluidly in conjunction with the runner's legs serves to reduce the energy needed to propel the runner forward. Furthermore, proper arm swing assists in speed production, power transfer, and maintaining foot cadence.

Proper arm swing requires that the arms move in synchronization with the legs on opposite sides of the body. In other words, the runner's left arm swings forward as the right leg is moving forward and vice versa. The counter movement of the opposing arm and leg operates to balance the runner, conserve energy, and propel the runner forward with momentum. The rhythm of the arms coordinates the efficiency and propulsion of the legs.

This synchronization of the arms and legs stabilizes the runner torso, minimizing rotation of the torso and directing runner energy into forward motion. Over-rotation of the torso results in wasted energy, thereby causing the runner to fatigue more quickly or run slower.

Methods and apparatuses are described for determining proper user torso (also referred to herein as the user "trunk") motion during running. Proper torso motion during running is important for several reasons. A proper torso motion, operating fluidly in conjunction with the runner's legs and arms serves to reduce the energy needed to propel the runner forward.

Proper torso motion requires that the user avoid unnecessary vertical displacement during the running stride. In other words, the runner should avoid an unnecessarily bouncy stride whereby the runner is wasting energy propelling himself or herself in an excessively upward direction instead of a forward direction. Unnecessary vertical displacement results in wasted energy, thereby causing the runner to fatigue more quickly or run slower.

Proper torso motion also requires that the user avoid unnecessary torso rotation during the running stride. Over-rotation of the trunk results in wasted energy, thereby also causing the runner to fatigue more quickly or run slower. Over-rotation of the trunk may cause delays in the runner arm swing in a proper forward and back motion, thereby causing a delay in the opposite leg. Again, this causes the runner to run slower. Correspondingly, problems with the runner arm swing and/or arm/leg synchronization may be identified by detecting unnecessary torso rotation. For example, excessive rotation of the runner arms about the user torso or a lack of arm/leg synchronization may cause the runner torso to rotate excessively.

Furthermore, the amount of torso motion allowed while still maintaining proper form may be dependent on user running speed. For this reason, in certain examples methods are apparatuses are described whereby whether the torso motion is determined to be unnecessary or excessive is based on a current measured user speed.

A proper arm swing should be rhythmic and similar to a pendulum, providing a source of balance, power, and rhythm. The amplitude of the arm swing should scale upwards or downwards depending on the runner speed and stride length. The movement should be a direct back and forth movement, without a rotational component about the user torso, sideways movements, or angled movements. The arm back and forth directional movement matches the leg back and forth directional movements. The angle of the lower arm and upper arm at the elbow should be approximately 90 degrees and may increase slightly as they are swung straight back. The increase of the angle at the elbow during take back allows for the opposite leg to complete its cycle of movement rearward.

The inventor has recognized that monitoring whether the user hands/wrists pass with close proximity to the user hips during the pendulum swing is advantageous for several reasons. First, when the arms are swung in the proper back and forth rhythm with the proper angle at the elbow, the user hand/wrist will pass in close proximity to the user hip in both the forward and reverse direction at the same proximity. As such, the determination that the user hands/wrists pass within close proximity to the user hips is a reliable indicator of proper arm swing and arm angle. The inventor has recognized that the runner is less likely to swing the arms rotationally about the user torso if the hands/wrists are kept in proximity to the sides of the user hips during the pendulum swing instead of higher towards the runner chest area. The proper back and forth pendulum swing (i.e., no rotation about the user torso) and elbow angle is difficult, if not impossible to achieve if the hands are positioned to the side of the chest during the midpoint of the back and forth swing instead of the side of the hip. Second, when the user hands/wrist are kept in close proximity to the user hips during the pendulum swing, this allows the runner to more easily maintain a hips-forward running position. One biomechanical stride defect found in many runners is often referred to as "overstriding," where the runner foot lands in front of the runner body's center of gravity instead of beneath it. In a biomechanically proper stride, the runner's foot should land closer beneath the hips as opposed to far in front of the hips. Running with a hips-forward running position reduces overstriding by enabling the runner foot to land closer beneath the hips.

In one example, a method for monitoring a user stride includes monitoring a user vertical displacement during a running stride, monitoring a user motion parameter associated with the running stride, and determining whether the user vertical displacement exceeds a threshold value, the threshold value dependent on the user motion parameter. In one example, the user motion parameter comprises a user horizontal displacement during the running stride. A vertical displacement/horizontal displacement ratio may be determined. In one example, the user motion parameter comprises a user speed during the running stride. The threshold value is adjusted upward when the user speed increases and is adjusted downward when the user speed decreases. In one example, the method further includes outputting an alarm indicating the user vertical displacement exceeds the threshold value. In one example, the method further includes monitoring a striding angle utilizing a torso mounted sensor.

In one example a system for monitoring a user stride includes a sensor system and a device. The sensor system is adapted to be worn on a user torso, and includes a first wireless transceiver. The device is adapted to be worn on a user and includes a second wireless transceiver configured to receive a sensor system output from the first wireless transceiver, a user interface, a processor, and a memory comprising a torso analysis application configured to process the sensor system output to determine a user torso motion during a running motion. For example, the user torso motion is a torso stride angle, vertical displacement or vertical acceleration, or torso rotation. In one example, the torso analysis application is further configured to determine whether the user torso motion exceeds a threshold value. An alarm may be output if the threshold value is exceeded. The threshold value may be specific to the user. In one example, the device further comprises a global positioning system unit configured to monitor a user speed, wherein the threshold value is dependent on the user speed.

In one example, a computer readable storage memory stores instructions that when executed by a computer cause the computer to perform a method for monitoring a user stride. The method performed includes receiving a sensor output associated with a movement of a user torso during a running motion, and analyzing the sensor output to identify an undesirable torso motion. In one example, the undesirable torso motion comprises a torso stride angle, a torso vertical displacement, a torso vertical acceleration, or a torso rotation in excess of a threshold value. In one example, the method further includes receiving a user speed data. The threshold value may be dependent on a user speed. The threshold value may be adjusted upward when the user speed increases and is adjusted downward when the user speed decreases.

FIG. 1 illustrates a system for athletic performance and technique monitoring being worn by a walker or runner 1 in one example. FIG. 1 shows a walking or running person 1 wearing a sensor unit 2 around his wrist and wearing athletic shoes to which a sensor unit 4 is attached. However, the sensor unit 4 may also be incorporated in the sole of the shoe or elsewhere on or within the shoe. The sensor unit 4 may also be attached directly to the foot of the person. The person 1 is also wearing a sensor unit 6 around his torso.

Sensor units 2, 4, and 6 are placed on or attached to person 1 directly or indirectly. For example, sensor units 2, 4, and 6 may be attached to or on, placed within, or otherwise integrated with worn shoes, accessories, clothing, or equipment. Sensor units 2, 4, and 6 may be mounted directly on runner 1 by adhesives, bands, straps, hooks, other mechanical connectors.

In some examples, the sensor unit 2 may be attached to the user's wrist in an enclosure which is similar to a watch and combined with other functionality such as timekeeping or with other sensors such the navigation device. In further examples, the sensor unit 2 may be attached to the user's arm using an enclosure similar to an armband and combined (i.e., integrated) with other devices such as a cellular phone, an audio device and/or the navigation device. The armband is particularly useful for cellular phones having larger, rectangular housings, including cellular phones such as "smartphones".

In some examples, the sensor unit 4 may be attached to the top of a user's shoe with removable fasteners such as clips.

In other examples, the sensor unit 4 may be inserted within the user's shoe, such as within a recess formed in the sole of the shoe.

In one example, the sensor unit 6 includes one or more sensors 50 (e.g., accelerometers) or other inertial sensors and may be attached to the user with a chest strap in an enclosure which may include other sensors such as a heart-rate monitor (HRM) sensor. In the example shown in FIG. 1, sensor unit 6 includes sensors 50*a* and 50*b* which are triaxial accelerometers mounted in parallel on both the left and right side of the runner 1 torso.

In further examples, the sensor unit 6 may be attached to the user's waist using a belt, clip, or other means. In one example, one of the sensors 50 is oriented in sensor unit 6 so that the vertical displacement of the user torso (i.e., along an axis running between the user foot and head) is monitored with each stride. In one example, this vertical displacement (i.e., the variation in height off of the running surface) of the user torso is compared to the stride length to generate a vertical displacement/horizontal displacement ratio. Advantageously, utilizing a torso mounted accelerometer reduces the complexity of calculating the vertical displacement of the user relative to a foot mounted sensor as the user torso does not move in a rearward direction at any time during striding. The vertical displacement/horizontal displacement ratio may be utilized to determine whether the user is undesirably exerting unnecessary energy in a vertical upwards direction for a given horizontal displacement. In a further example, the vertical displacement may be compared to a horizontal velocity or horizontal acceleration. In a further example, a vertical acceleration/horizontal acceleration ratio is calculated.

For example, if the vertical displacement/horizontal displacement ratio exceeds a predetermined threshold value, an audible alarm may be output to the user. In one example, the threshold value is specific to the user. For example, the system including sensor unit 4 and sensor unit 6 may enter a learning/teaching mode whereby the user runs in the desired form for a test interval and the target vertical displacement/horizontal displacement ratio is measured. For example, during the learning mode, the runner may focus on avoiding unnecessary excess vertical displacement or vertical acceleration. In a further example, the threshold ratio value is determined using test measurements of other runners or established norms and stored by the system prior to use by the runner.

In a further example, the measured motion parameter utilized is the vertical displacement by itself. For example, if the vertical displacement exceeds a predetermined threshold value, an audible alarm may be output to the user. In one example, the threshold value is specific to the user. For example, the system including sensor unit 6 may enter a learning mode whereby the user runs in the desired form for a test interval and the target vertical displacement is measured. In a further example, the threshold value is determined using test measurements of other runners or using established norms and stored by the system prior to use by the runner. In yet another example, the threshold value is set to a specific amount. For example, the threshold value may be set to approximately between 2 to 4 inches. In yet another example, the threshold value is adjusted in real-time based upon the speed of the user. For example, as the speed of the user increases while running, the threshold value may be adjusted in an upward direction. As the speed of the user decreases while running, the threshold value may be adjusted in a downward direction. As described elsewhere herein, threshold values may be set or determined in a variety of ways, including a learning mode whereby values are set specific to the user and/or preset during manufacturing based on tests of other runners, such as elite runners known to perform at high levels, or based on theoretical calculations.

In one example, the vertical threshold is adjusted upward as the user increases speed in the direction of locomotion and adjusted downward as the user decreases speed. Again, the amount of adjustment maybe set/calibrated specific to the user based on the learning mode tests at different speeds and/or pre-set during manufacturing. The average vertical displacement/horizontal displacement ratio or the average vertical displacement over a given time or distance interval may be calculated and output to the user in real time or during subsequent workout analysis.

Sensor units 2, 4, and 6 are operable to sense data associated with the athletic performance such as physical or physiological data. For example, sensor unit 4 may output a signal which is processed to determine step count, step impact, velocity, jump height, distance and other data associated with walking and running activities.

Sensor unit 2 may output a signal which is processed to determine arm motion of runner 1. Sensor unit 2 may also be operable to sense global positioning system (GPS) data, such as location and altitude data. Sensor unit 2 may use GPS satellites or other means, including cellular towers, to determine location. Sensor unit 6 may also monitor time data. Sensor unit 6 may include sensors operable to sense heart rate, temperature and movement in the horizontal and vertical direction.

In further examples, any number of sensors may be provided to sense any desired type of athletic performance information. Furthermore, as used herein, the term "sensor" may refer to one or more sensors. Sensor of varying types may be placed at the same desired location on runner 1. For example, sensor unit 2 may include both an inertial sensor and a GPS locator. Sensor unit 6 may include both an inertial sensor and a heart rate sensor.

Sensor units 2, 4, and 6 are operable to communicate wirelessly amongst themselves. In the example shown in FIG. 1, sensor unit 6 is in communication with sensor unit 2 via a wireless link 3 and sensor unit 4 is in communication with sensor unit 2 via a wireless link 5.

Sensor unit 2 may also be configured to communicate with computing devices, exercise devices, navigation devices, sensors, and any other enabled devices through a communication network, such as a local area network, a wide area network, or the Internet. Such communication may occur via wired or wireless links.

In the example shown in FIG. 1, sensor unit 2 for has been incorporated into a wrist-worn device. For example, wrist worn device may assume a watch form factor having some form of visual display and audio output. Data collected by sensor unit 4 and sensor unit 6 are transmitted to sensor unit 2 (i.e., the wrist worn device) for processing and/or output together with data collected by sensor unit 2. The collected sensor data is processed, stored, and/or displayed at sensor unit 2.

In a further example, data collected by sensor units 2, 4, and 6 are transmitted to an electronic device for processing, where the electronic device need not itself have a sensor. For example, the electronic device may be an MP3 or other type of digital music player, watch, handheld computing device, cellular telephone, or any other device capable of displaying information or outputting audio. The electronic device may process the received sensor data and output associated information to the user via a user interface output such as a LCD display. The electronic device may be attached to the runner's body in any manner similar to that of a sensor so that it is easily carried, moved, heard, or viewed during running. Utilizing the user interface 7, real-time feedback is provided as to the user's arm/opposite leg synchronization, arm rotation across the torso, and vertical/horizontal displacement ratio.

Figure 2:
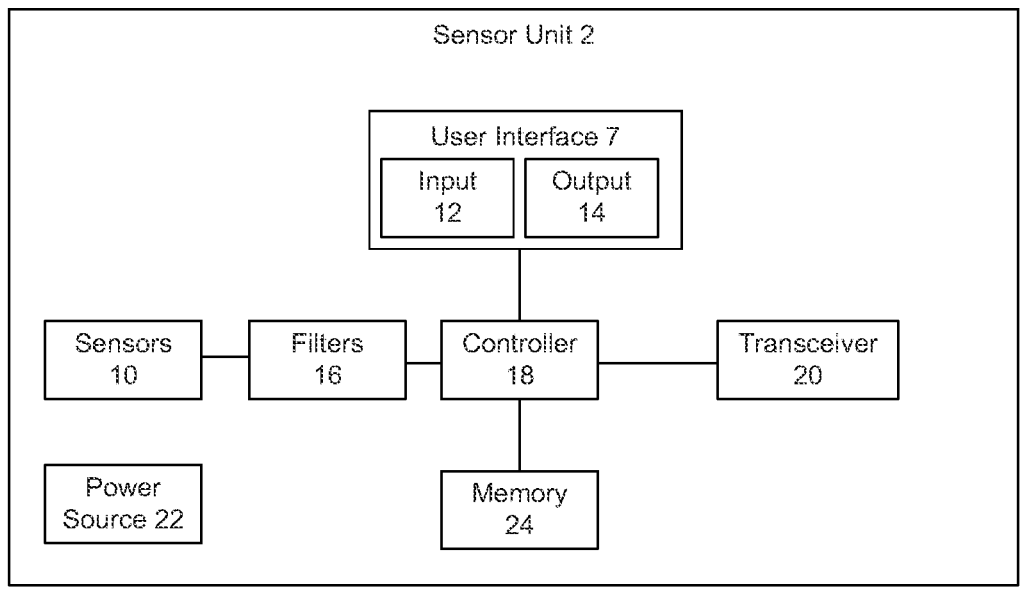
FIG. 2 illustrates a simplified block diagram of a wrist worn component of the system shown in FIG. 1.

FIG. 2 illustrates a simplified block diagram of a wrist worn component, sensor unit 2, of the system shown in FIG. 1. Although shown worn on the wrist, sensor unit 2 may be worn on the user's forearm or arm in further examples. Sensor unit 2 includes a user interface 7. User interface 7 includes an input device 12 and an output device 14. For example, input device 12 may be one or more buttons, switches, a touch bezel, or a touch screen.

Output device 14 may include speakers for outputting audio and a visual display screen. The output device 14 may also include a vibrate element to notify users of information via mechanical vibration. Although shown integrated with sensors 10 within sensor unit 2, in further examples, the user interface 7 can be positioned separately from any sensor devices. The user interface 7 may also include various processing and memory devices to facilitate its functionality. The user interface 7 is operable to receive inputs from the user to control the functionality of the sensor unit 2 and elements associated therewith.

Output device 14 enables users to receive real-time feedback concerning the estimated motion parameter and associated information. For instance, the user interface 7 may present the currently estimated motion parameter, such as degree of synchronization between the user arm and opposite user leg, current stride speed and distance, and/or information associated therewith or with other motion parameters, such as total distance or combinations thereof.

In various examples, the user may configure the sensor unit 2 utilizing the user interface 7 to monitor estimated motion parameters and alert the user through the output device 14 when one or more estimated motion parameters either fall within or fall outside a user-defined condition such as an acceptable parameter range, threshold, or variance.

Sensor unit 2 includes one or more sensors 10. In one example, sensors 10 include one or more accelerometers. In one example, the accelerometer is a tri-axial accelerometer. In one example, the one or more accelerometers are linear accelerometers. In a further example, sensors 10 include a gyroscope in addition to an accelerometer.

Sensor unit 2 also includes filters 16, controller 18, transceiver 20, power source 22, and memory 24. Controller 18 may include one or more signal processors. In one example, power source 22 is a battery, which may be rechargeable or not rechargeable.

Memory 24 may include any computer-readable memory or combination of computer-readable memories operable to store data for use by the controller 18. For instance, the memory may be operable to store acceleration data, motion parameter metric data, statistical data, motion parameter data, filtering data, configuration data, or any combination thereof.

The sensors 10, filters 16, and controller 18 may be integrated together or form discrete elements that may be associated with each other. The controller 18 is operable to analyze measurements provided by the sensors 10 to estimate parameters corresponding to one or more parameter types.

Controller 18 and its included processors are generally operable to couple with the one or more sensors 10 to estimate a motion parameter corresponding to a motion parameter type. The controller 18 may include various analog and digital components operable to perform the various functions discussed herein. For example, the controller 18 may include a microprocessor, a microcontroller, a programmable logic device, digital and analog logic devices.

The controller 18 additionally utilizes information acquired from sensors other than the one or more sensors 10 via wireless links using transceiver 20 to enable real-time comparison of information generated by various sensors in the system. For example, the controller 18 receives information from sensor unit 4 and sensor unit 6 to generate one or more motion parameters using such information.

Similarly, the controller 18 may couple with other sensors to acquire any type of information, For example, to acquire additional information, the controller may couple with, and/or include, gyroscopes, altimeters, compasses, and pressure sensors, and other inertial sensors, or any combination thereof, disposed at sensor unit 2, 4, 6, or elsewhere.

Utilizing various signal processing algorithms, the controller 18 may analyze and compare measurements provided by sensors 10, sensors 40, and sensors at sensor unit 6. For example, by identifying and/or comparing the minimum(s), maximum(s), period, frequency, waveform, rate of change, combinations thereof, and the like, the processing system 16 may process the acceleration signatures to determine one or more motion parameters. Controllers at each sensor unit 4 and 6 may implement similar signal processing algorithms.

In a further example, sensor unit 2 includes a navigation device adapted to provide geographic location information. The navigation device may include a GPS receiver or may use cellular or other positioning signals instead of the GPS to determine geographic position and generate navigation information. For example, the navigation device is operable to determine speed, current and previous locations, bearing and heading, and altitude. In further examples, the various components of the sensor unit 2 may be housed integrally or separately in any combination.

In one example, undesirable arm swing in a circular direction across the front of the user torso (as opposed to the desirable swing direction maintained back and forth along an axis or plane defined by the direction of movement) is measured with two accelerometers, a triaxial accelerometer, or a gyroscope housed within sensor unit 2. In one example, measured translational accelerations are used to compute angular acceleration which can be doubly integrated to obtain the amount of arm swing in a plane substantially perpendicular to the direction of travel.

Figure 3A:
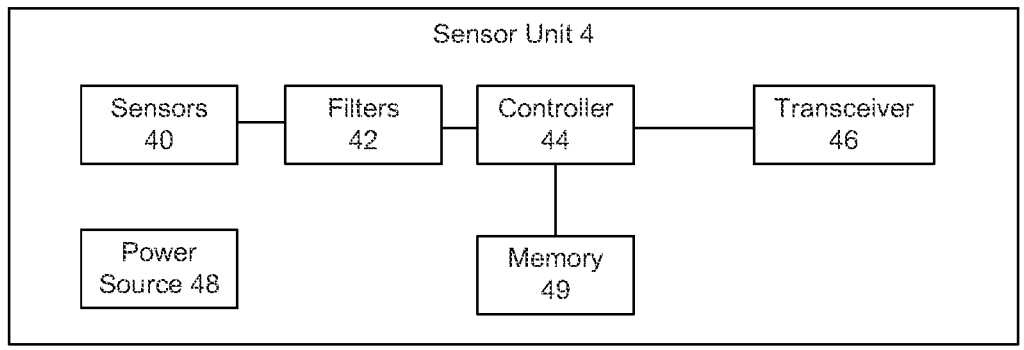
FIG. 3A illustrates a simplified block diagram of a foot mounted component of the system shown in FIG. 1.

FIG. 3A illustrates a simplified block diagram of a foot mounted component, sensor unit 4, of the system shown in FIG. 1. Sensor unit 4 includes sensors 40, filters 42, controller 44, transceiver 46, power source 48, and memory 49. Controller 44 may include one or more signal processors. In one example, power source 48 is a battery.

Sensor unit 4 includes one or more sensors 40. In one example, sensors 40 include one or more accelerometers. In a further example, sensors 40 include a gyroscope in addition to an accelerometer. In one example, the accelerometer is a tri-axial accelerometer. In one example, the one or more accelerometers are linear accelerometers.

The sensors 40, filters 42, and controller 44 may be integrated together or form discrete elements that may be associated with each other. The controller 44 is operable to analyze measurements provided by the sensors 40 to estimate parameters corresponding to one or more parameter types.

The one or more sensors 10 and 40 are each operable to measure an acceleration and generate an acceleration measurement corresponding to the measured acceleration. The acceleration measurement may be embodied as a signal operable to be utilized by the filters 16 and 42 and/or controllers 18 and 44.

In some embodiments, one or more of the sensors 10 and 40 may be operable to output an analog signal corresponding to an acceleration measurement. For instance, each accelerometer may output an analog voltage signal that is proportional to measured accelerations.

However, the one or more sensors 10 and 40 may include any digital and analog components operable to generate a signal corresponding to a measured acceleration. Thus, in some embodiments, one or more of the sensors 10 and 40 are operable to output a digital signal representing measured accelerations. Further, in some embodiments, one or more of the sensors 10 and 40 may comprise linear accelerometers.

In some embodiments, more than one of the sensors 10 and 40 may be integrated into the same integrated circuit package to allow the single package to provide acceleration measurements along more than one axis. Sensors 10 and 40 may each include two or more accelerometers each operable to output a signal corresponding to a measured acceleration.

In some examples, sensors 10 and 40 each include two accelerometers adapted to measure accelerations in two directions separated by an angle greater than zero degrees and each provide a signal corresponding to the measured acceleration. In some examples, sensors 10 and 40 may each include at least three accelerometers adapted to measure accelerations in three directions each separated by an angle greater than zero degrees and each provide a signal corresponding to the measured acceleration. In some embodiments, the three accelerometers may be oriented in a mutually perpendicular configuration. In one example, sensors 10 and sensors 40 are each a triaxial accelerometer. However, sensors 10 and 40 may include any number of accelerometers, including a single accelerometer positioned in any configuration to provide acceleration measurements.

Transceiver 20 and transceiver 46 are configured for wireless communication using various RF protocols. For example, transceiver 20 and transceiver 46 may communicate utilizing Bluetooth, ANT, and/or any other wireless protocols.

The filters 16 and 42 are operable to couple with the one or more accelerometers and filter acceleration measurements and/or signals corresponding to acceleration measurements. The filters 16 and 42 may include analog and digital components operable to filter and/or provide other pre-processing functionality to facilitate the estimation of motion parameters by the processors at controllers 18 and 44. In various examples, the filters 16 and 42 are operable to filter signals provided by the one or more accelerometers, or signals derived therefrom, to attenuate perpendicular acceleration, to compensate for gravity, and/or to minimize aliasing. The filters 16 and 42 may include discrete components for performing each of these filtering functions or use the same components and hardware for these, and other, filtering functions.

The anti-aliasing provided by the filters 16 and 42 generally reduces or prevents aliasing caused by sampling of the signals provided by, or derived from, the one or more accelerometers. In some embodiments, the filters 16 and 42 include a relatively wideband filter designed to attenuate signal frequencies in excess of one-half of the sampling frequency used in any subsequent analog-to-digital conversions provided by the controllers.

The filters 16 and 42 may include any analog and digital components for filtering signals and measurements, including passive and active electronic components, processors, controllers, programmable logic devices, digital signal processing elements, combinations thereof, and the like. The filters 16 and 42 may also include an analog-to-digital converter to convert analog signals provided by the one or more accelerometers to digitize signals for use by the processors at controllers 18 and 44. The filters 16 and 42 may also include conventional pre-sampling filters. In some examples, the low-pass filter 18 may be an adaptive filter operable to employ static and/or varying cut-off frequencies between about 0.5 Hz and 10 Hz.

In one example, sensor unit 6 worn about the user chest contains substantially similar components to that of sensor unit 4 illustrated and described in reference to FIG. 3A. In one example, sensor unit 6 includes a heart rate monitor to advantageously benefit from its position across the user chest.

Figure 3B:
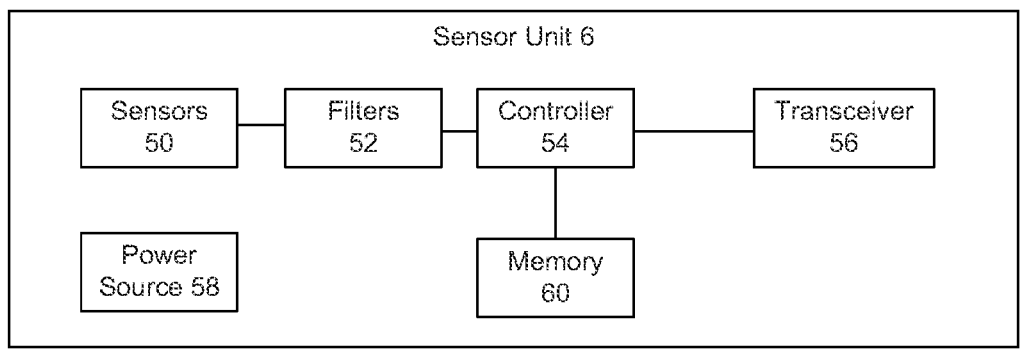
FIG. 3B illustrates a simplified block diagram of a torso mounted component of the system shown in FIG. 1.

FIG. 3B illustrates a simplified block diagram of a torso mounted component, sensor unit 6, of the system shown in FIG. 1. Sensor unit 6 includes sensors 50, filters 52, controller 54, transceiver 56, power source 58, and memory 60. Controller 54 may include one or more signal processors. In one example, power source 58 is a battery. Operation of the various components of sensor unit 6 are substantially similar to that of the similarly named components of sensor unit 4 described above with respect to FIG. 3A.

Sensor unit 6 includes one or more sensors 50. In one example, sensors 50 include one or more accelerometers. In one example, the sensors 50 include a gyroscope. In one example, the sensors 50 include a heart rate monitor. In one example, the one or more accelerometers include one or more tri-axial accelerometers. In one example, the one or more accelerometers are linear accelerometers. In one example, sensors 50 include a pair of sensors 50a and 50b which are parallel spaced triaxial accelerometers as shown in FIG. 1.

Depending upon the location of the sensor, one or more motion analysis algorithms may be used to determine one or more motion parameters. Sensor unit 2, sensor unit 4, and sensor unit 6 may store in memory a database of motion analysis algorithms corresponding to various combinations of attachment positions and motion classifications as appropriate. For example, the memory may include motion analysis algorithms for: foot, chest, and arm attachment locations.

Utilizing one or more selected motion analysis algorithms and acceleration signals provided by the sensors, the sensor unit 2, sensor unit 4, or sensor unit 6 may estimate, calculate, identify, or otherwise determine one or more motion parameters. For example, the motion parameter may correspond to direction of movement of a user leg or arm in any direction, degree of synchronization of movement of an opposite user arm and leg, vertical displacement of the user torso (and effectively, the user head), rotation of the user torso, side to side (i.e., left to right or horizontal) movement of the user torso in a plane centered between the front and back of the runner substantially perpendicular to the direction of locomotion, rotation of the user arm about the user torso or movement of the user arm in a side to side direction, stride speed, acceleration, velocity, stride distance, total distance, gait efficiency, energy, maximum impact, speed variability, strike time, steps, step cadence (e.g., number of steps per minute, also referred to herein as "stride rate" herein) and combinations thereof, or any other motion parameter described herein. Furthermore, the motion parameter determined may correspond to any parameter associated with the motion of the user. In one example, motion parameters are calculated at each individual sensor unit 2, sensor unit 4, and sensor unit 6. In a further example, sensor unit 2 receives data from sensor unit 4 and/or sensor unit 6 and calculates motion parameters.

In one example, the output of sensors 40 at sensor unit 4 is processed to determine the time at which a stride begins and ends by determining when a runner's foot impacts the ground, when a runner's foot leaves the ground, and when a runner's foot is stationary relative to the ground. By analyzing various changes in measured accelerations, the controller 44 or controller 18 may compute the stride direction and duration and information corresponding thereto, such as stride frequency. The stride frequency may represent the number of strides per second or other indications of the rate of stride.

In various embodiments, the controller 18 is operable to compute the motion parameter metrics and/or estimate the motion parameters for each detected stride to facilitate the accurate analysis of movement, where the motion parameters are associated with sensor unit 2, sensor unit 4, and/or sensor unit 6. Alternatively, motion parameter metrics are calculated for each detected stride at sensor unit 2, 4, and 6, respectively.

In one example, sensor units 2, 4, and 6 are accelerometer-based sensor units. Sensor units 2, 4, and 6 each include one or more accelerometers and an amplifier circuit (including a high-pass filter integrated therein). The accelerometer or accelerometers in each unit may comprise any of numerous devices or circuits capable of detecting acceleration of the body part to which the sensor unit is attached and produce an output signal in response thereto, and the invention is not limited to the use of any particular type of accelerometer. In further examples, the accelerometer may be replaced with other suitable devices which may alternatively be used Sensor units 2, 4, and 6 include accelerometers arbitrarily oriented relative to the direction of user motion for generation of a signal corresponding to user motion. Sensors may be placed in any location or combination of locations on his or her body.

In one example, the accelerometers are piezo-electric accelerometers, such as those manufactured by Murata or Analog Devices, Inc. The sensor units include amplifiers which amplify the acceleration signal from the accelerometer to a level suitable for an analog-to-digital converter (A/D converter or ADC) which converts the amplified analog acceleration signal to a digital signal. The digital signal is supplied to a microprocessor which performs the analysis of the waveform of the acceleration sensor signal, the computation of the speed, stride length and other parameters of the running person. The electronic components necessary to perform the functions of the sensor unit 2, 4, and 6 may be mounted on a small printed circuit board, which is placed in a housing to be attached to the desired runner body part.

The example system shown in FIG. 1 includes a sensor unit 4 system shown in FIG. 3A for sensing and transmitting some type of athletic performance data. More specifically, in this example structure, athletic performance data (e.g., physical or physiological data associated with an athletic performance) is sensed by sensor(s) 40, and data from these sensor(s) is sent to the sensing system's processing system, e.g., a microprocessors at controller 44, which optionally may cause the data to be stored (e.g., in a storage system or memory 49), further processed, etc. A power source 48 may be provided to operate the various components of the sensor unit 4 system, such as the sensors 40, the controller 44 and associated microprocessors, the transceiver 46, memory 49, and/or any other necessary or desired components. If desired, the microprocessor on board the sensor unit 4 system, if any, may process the sensor data, change its form or format, or otherwise manipulate the data prior to sending it on to other parts of the system, such as to sensor unit 2.

At an appropriate or desired time (e.g., when a data request is received, periodically, automatically, upon user demand, etc.), the sensor unit 4 system may send at least some portion of its data (e.g., raw data directly from one or more of the sensors, data derived at least in part from the raw data, etc.) to the sensor unit 2, illustrated in FIG. 2, for further processing and/or eventual output to a user via user interface 7. This may be accomplished, for example, as shown in FIG. 1, via a wireless data transmission system (e.g., from wireless data transfer or transceiver element 46 in the sensor unit 4 system to wireless data receiving element transceiver 20 in the sensor unit 2) or in any other desired manner without departing from this invention. Any desired wireless protocol, broadcast protocol, or other data transmission protocol may be used without departing from the invention.

Once received at the sensor unit 2, the athletic performance data may be further processed, if necessary or desired, and then supplied to the processing system (e.g., a microprocessor at controller 18) of the sensor unit 2. This may be accomplished at any suitable desired time or timing (e.g., when a data request is received, automatically, periodically, on user demand, etc.) based on the measured motion parameter without departing from this invention. From there, the data may be further processed, if necessary or desired, and then sent to an output device in a form suitable for output to a user (e.g., in audio, video, and/or alphanumeric form, etc.).

Figure 4:
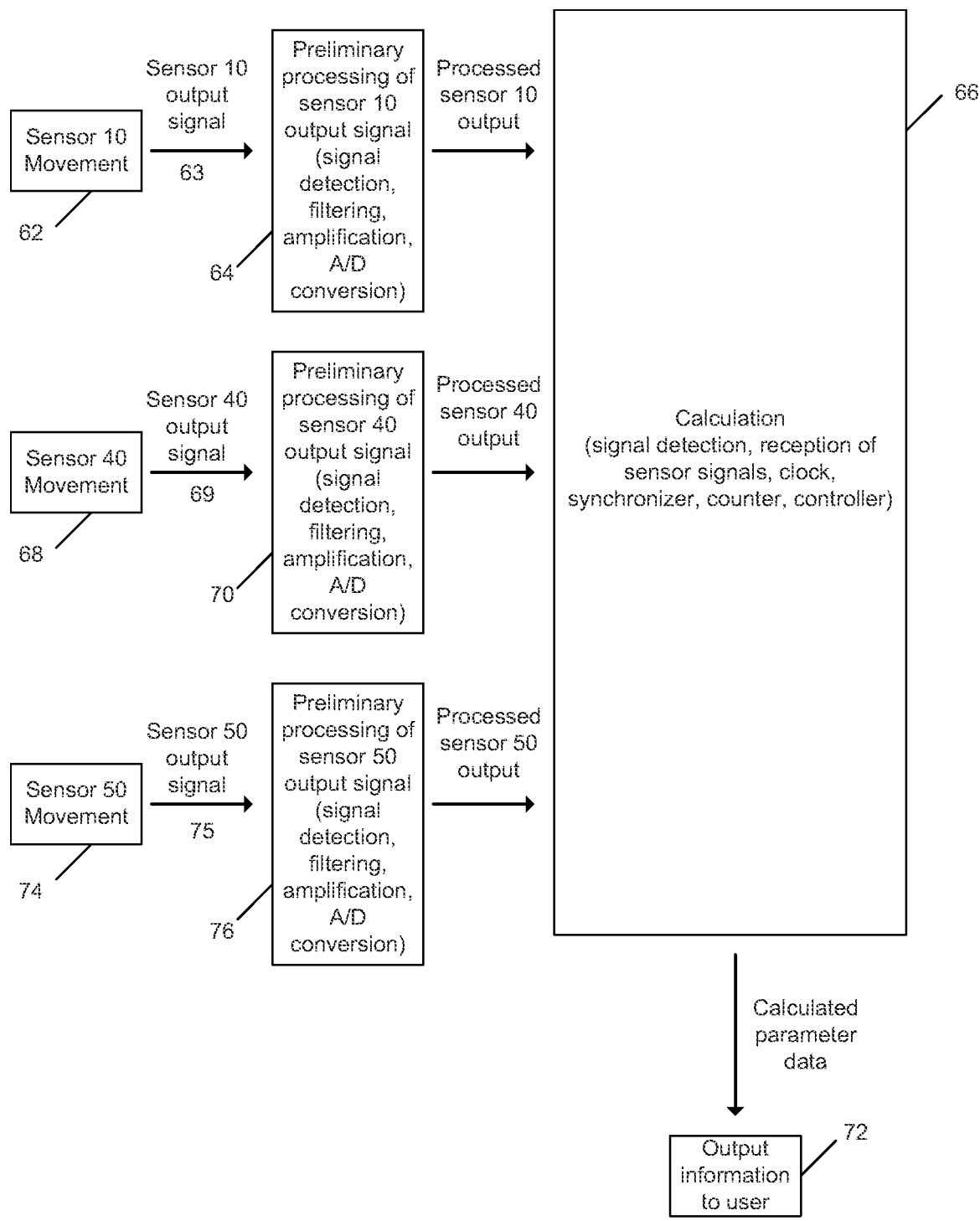
FIG. 4 illustrates an example of an athletic performance monitoring arrangement.

FIG. 4 illustrates an example of an athletic performance monitoring arrangement. During operation, sensor 10 movement 62 results in a sensor 10 output signal 63 which is sent to preliminary signal processing 64. In one example, preliminary signal processing 64 includes amplifying, filtering, signal detection, and transmission. Following preliminary signal processing 64, a processed sensor 10 output is sent to calculation unit 66 for further processing.

Similarly, sensor unit 40 movement 68 results in a sensor unit 40 output signal 69 which is sent to preliminary signal processing 70. In one example, preliminary signal processing 70 includes amplifying, filtering, signal detection, and transmission. Following preliminary signal processing 70, a processed sensor unit 40 output is sent to calculation 66 for further processing.

Similarly, sensor unit 50 movement 74 results in a sensor unit 50 output signal 75 which is sent to preliminary signal processing 76. In one example, preliminary signal processing 76 includes amplifying, filtering, signal detection, and transmission. Following preliminary signal processing 76, a processed sensor unit 50 output is sent to calculation 66 for further processing.

Calculation unit 66 receives multiple sensor output signals for calculating various desired motion parameters as described herein. Calculation 66 includes one or more signal receivers for receiving the sensor signals associated with the measurement variable from sensors 10, sensors 40, sensors 50, or any other system sensors. In certain examples, data from only select sensors is received and processed, depending on the desired motion parameter to be monitored. The one or more signal receivers also receive other information. Calculation unit 66 also includes signal processing for processing all of the received information. In operation, calculation unit 66 may perform processing functions including reception of sensor signals, clocking, synchronization, counting, timing, and signal detection.

The athletic performance monitoring arrangement illustrated in FIG. 4 includes processing to determine the motion parameters described herein. In one example, the determination of whether the runner arm and leg motions are synchronized are determined as described below in reference to FIGS. 5-7 utilizing the accelerometer output signals. Calculated motion parameter data is output to user 72 as set by the user via a user interface.

In various examples, the essential functions of the performance monitoring and measuring arrangement described can be implemented using separate components, integrated circuits, ASIC circuits, software or any combination of these. In one example, the software is stored at memory 24 and executed by controller 18 to perform functions as described herein. Various functions can be distributed among several components or performed at a single component as desired.

Figure 5:
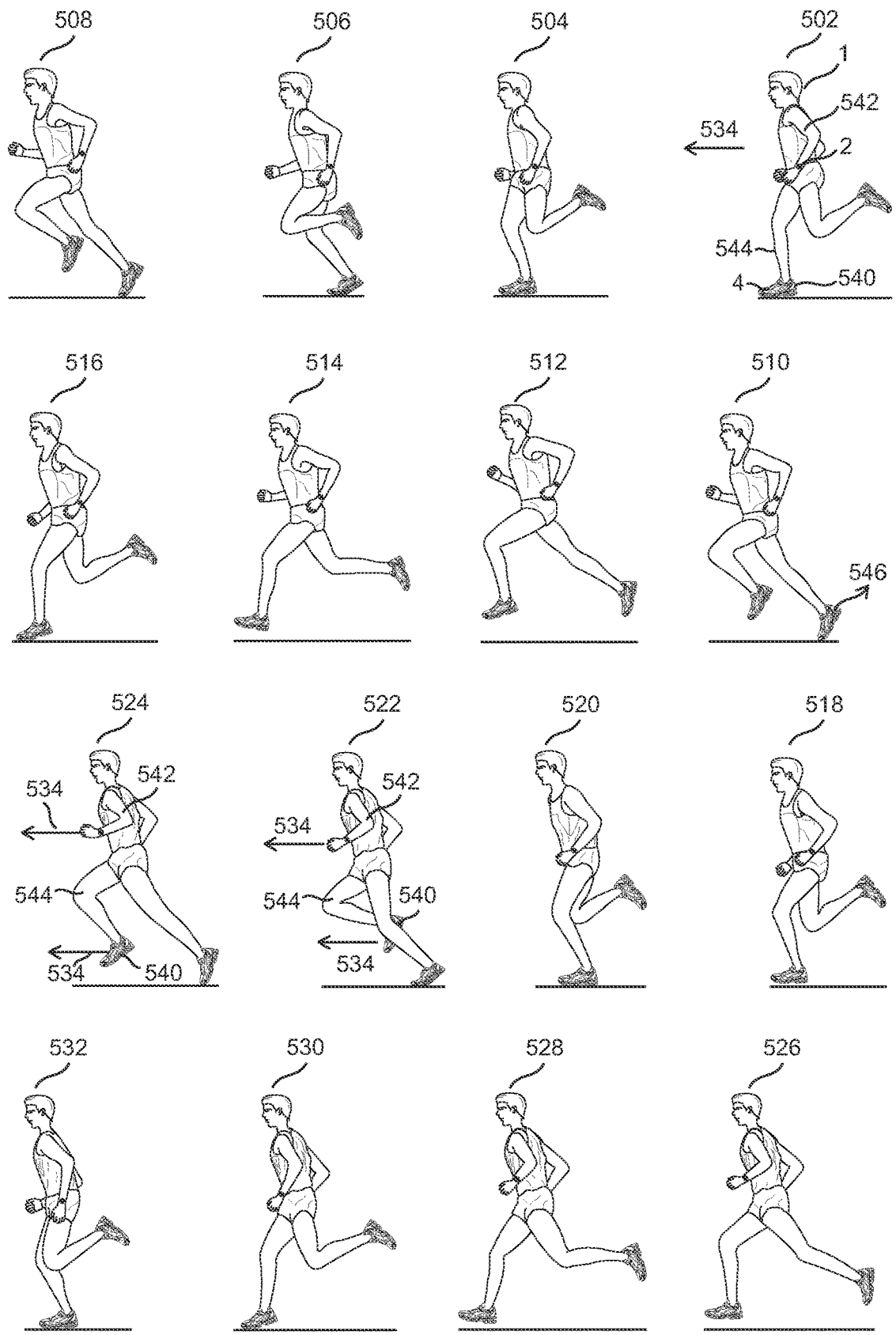
FIG. 5 illustrates a running progression of a runner wearing the system for athletic performance monitoring in one example.

FIG. 5 illustrates a running progression of a runner wearing the system for athletic performance monitoring in one example. FIG. 5 shows a running person 1 wearing a right shoe 540 with built-in sensor unit 4. The arrow 534 indicates a forward direction of acceleration of the shoe 540 along the line between the nose and heel of the shoe 4. The arrow 534 indicates a forward direction of acceleration of the sensor unit 2 (i.e., the runner left arm 542). As shown in FIG. 5, the forward direction is the direction in which runner 1 is running. The sensor units 2 and 4 should be mounted and oriented to be sensitive in the direction indicated with the arrows in FIG. 5. For example, the sensor unit 4 comprises an acceleration sensor unit 4 mounted in such a way that it senses acceleration in a direction substantially parallel to a line between the nose and the heel of the shoe 540.

In the running progression shown in FIG. 5, various time progressive snapshots 502 through 532 of the runner 1 are shown. The runner 1 is wearing a sensor unit 2 in the form of a wristwatch on a left arm 542 and is wearing sensor unit 4 on a right leg 544. In a further example, the runner 1 may wear sensor unit 2 on a left arm and wear sensor unit 4 on a right leg. In this example, sensor unit 2 and sensor unit 4 are worn are worn on opposite sides of the body (i.e., right side versus left side). Thus, if sensor unit 2 is worn on a right arm, sensor unit 4 is worn on the left leg. If sensor unit 2 is worn on a left arm, sensor unit 4 is worn on a right leg.

At snapshot 510, the runner right shoe 540 is or has just left the ground, referred to also as "toe-off" event, in a rearward direction 546 (i.e., a direction opposite the forward running direction) and upward direction. Overlapping with the rearward and upward direction of the right shoe 540, the runner left arm 542 is swung in a rearward direction (i.e., a direction opposite the forward running direction).

At snapshot 520, the runner right shoe 540 has reached its maximum rearward back kick height and is about to be begin its swing forward in the forward direction 534. At snap shot 522, the runner right shoe 540 is moving forward in forward direction 534, toward its maximum forward acceleration. Overlapping with the forward direction of the right shoe 540, the runner left arm 542 is swung in the forward direction 534.

At snap shot 532, the runner right shoe 540 has landed on the running surface, referred to as a foot strike event, returning to the position shown in the start of the stride in snapshot 502. Snap shot 532 illustrates the completion of one stride of the user right foot began at snap shot 502. During locomotion the runner will then repeat the sequence shown in snap shots 502-532.

In the runner stride between a toe-off event and a foot strike event for a given foot, the foot is in the air for a "foot in air" amount of time. In the runner stride after foot strike but before toe-off, the foot is on the ground for a "foot on ground" amount of time. Snapshots 502 to 532 show a sequence in which the runner left arm 542 and right leg 544 are desirably substantially synchronized in direction, with overlapping movement in either the rearward direction or forward direction.

Systems and methods described herein are operable to detect whether left arm 542 and the right leg 544 are desirably synchronized in either the rearward or forward direction or whether they are substantially unsynchronized such that the left arm 542 is substantially moving forward while the right leg 544 is moving rearward, or vice versa. The degree of synchronization may be measured. For example, the amount of overlap between movement of both left arm 542 and right leg 544 in the same direction is monitored. A threshold amount of overlap may be set, above which synchronization is determined to be present and below which synchronization is determined not to be present.

In one example, the threshold amount of overlap is set using the learning/calibration mode described above whereby a user runs with a desired synchronization between the opposite arm and leg and the amount of overlap in the same direction is measured and set as the threshold value or used as the basis for setting the threshold value. For example, the actual threshold value used during regulation operation (i.e., non-learning mode) is set slightly below the measured threshold value.

Figure 6:
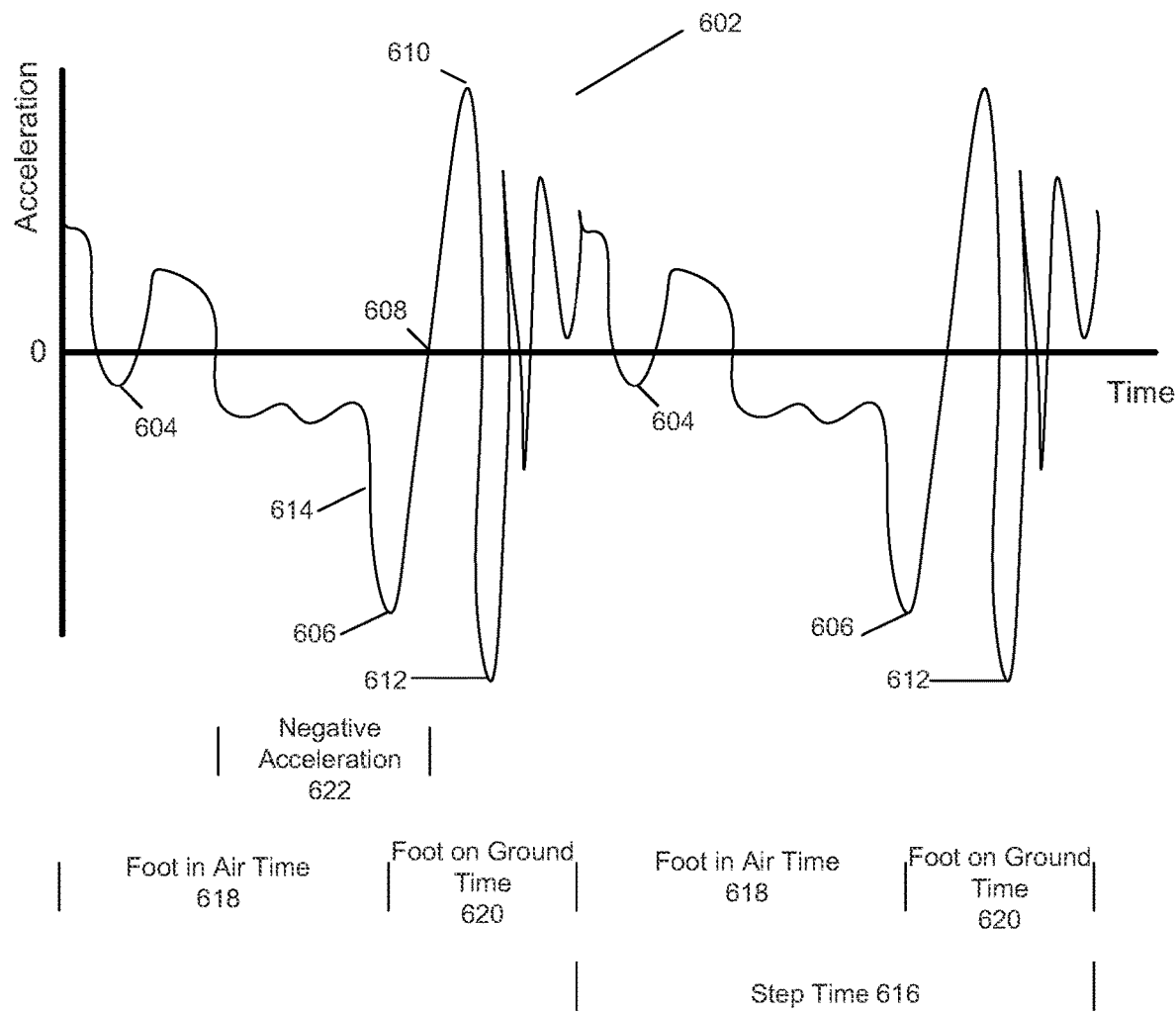
FIG. 6 illustrates a graph showing a typical output signal of a sensor mounted on a runner foot during locomotion.

FIG. 6 illustrates a graph showing an exemplary typical output signal of a sensor mounted on a runner foot during locomotion. FIG. 6 shows an example of an amplified accelerometer output signal 602 that may be provided by the sensor unit 4 to the controller 44 when the runner 1 is in locomotion on foot. Output signal 602 may be converted into digital values.

As also shown in FIG. 6, the signal 602 may fluctuate dynamically in response to movement of the user's foot that occur when the user is walking or running. When the level of the signal 602 is greater than zero, this indicates that the accelerometer is sensing a positive acceleration along the acceleration sensing axis, and when the level of the signal 602 is less than zero, this indicates that the accelerometer is sensing a negative acceleration along the acceleration axis. The acceleration signal 602 is subjected to an algorithm executed by a microprocessor.

Particular characteristics of the signal 602 may be identified which are indicative of particular occurrences during each footstep. In one example, signal 602 is analyzed to (1) identify occasions when the user's foot first leaves the walking or running surface after having been in contact with the ground during a footstep (e.g., a "toe-off" events), (2) to identify occasions when the user's foot first impacts the ground after having been airborne (e.g., "foot strike" events), (3) to identify occasions when the user's foot is airborne, (4) to identify occasions when the user's foot is moving forward in the direction of locomotion, and (5) to identify occasions when the user's foot is moving rearward opposite the direction of locomotion.

The relatively small negative peaks 604 indicate the beginning of a stride which corresponds to the moment the shoe leaves the ground and starts moving rearward and upward (i.e., a toe-off event). The zero crossing 608 after the large negative peak 606 indicates the end of the stride which corresponds to the moment the shoe lands on the ground again (i.e., a foot strike event). Following foot strike, but before toe-off, the user foot is in contact with the ground for a period of time ("foot on ground time"). Following toe-off, but before foot-strike, the user foot is in the air ("foot in air time" or simply "air-time"). The stride time may be measured as the time between zero crossings after the large negative peak 606.

In one example, an algorithm identifies the beginning and end of a stride. The signal 602 is analyzed to find the relatively small negative peaks 604 in the signal which are indicative of the beginning of a stride and the relatively large negative peaks 606 just before the zero crossings 608 which are indicative of the end of a stride. For example, negative peaks are detected by monitoring when the first derivative of the acceleration signal changes from negative to positive. Further, a smoothed version of the acceleration signal 602 is constantly monitored. Finally two minima are logged, the overall minimum and a local minimum somewhere around the smaller negative peak 604 at the moment the foot leaves the ground. When, at a certain negative peak, the value of the acceleration signal is below a certain limit, the peak is detected. This limit lies half way between the smoothed signal and the minimum.

In one example, toe-off events are identified by monitoring the signal 602 for characteristics that indicate a toe-off event may have potentially occurred. For example, one characteristic in the signal 602 indicative of a potential toe-off event is a large inflection in the signal 602. In this example, inflections in the signal 602 are monitored to identify and to continuously update the identification of a largest inflection to occur in the signal 602 subsequent to the most recent foot-strike event.

In a further example, toe-off events are identified by monitoring the signal 602 for characteristics that indicate the foot is definitely airborne. Such characteristics are referred to herein as the signal's "air signature". The air signature may, for example, be an identified period of relative smoothness substantially free from sharp transitions in the signal 602. When it is determined that the foot is airborne (i.e., an air signature is identified), the most recently identified potential toe-off event is identified as the actual toe off event. The end of the stride can be recognized comparatively easily in the acceleration signal 602, because the hard strike of the foot's landing on the ground causes high acceleration peaks 610 and 612, for example.

In one example, foot-strike events may be identified by monitoring the signal 602 for sudden, sharp inflections following the relatively smooth condition of the signal 602 generated while the foot is airborne. In one example, characteristics of the signal 602 are monitored to determine whether the signals satisfy at least one of a plurality of predetermined criteria consistent with the occurrence of a foot-strike event. In one example, after an air signature of the signal 602 has been identified (i.e., it has been determined that the foot of the user is airborne), a subsequent sharp, positive peak 610 in the signal 602 is one characteristic in the signal 602 that is indicative of the foot of the user impacting the running surface.

In one example, periods in which the user's foot is moving forward in the direction of locomotion such as in a stepping motion may be identified by monitoring the signal 602 for: (a) characteristics that indicate the foot is airborne combined with period of negative acceleration 622 with an increasing negative acceleration 614 leading to a large negative peak 606, or (b) characteristics that indicate a foot strike has occurred, where a period of negative acceleration prior to the foot strike indicates movement in the forward direction, or (c) a period of negative acceleration prior to the relatively large negative peaks 606 just before the zero crossings 608.

In one example, periods in which the user's foot is moving rearward in a backward and upward direction following initial toe-off may be identified by monitoring the signal 602 for: (a) characteristics that indicate the foot is airborne combined with period of positive acceleration, or (b) the period of time immediately following toe-off, but prior to movement of the foot in an identified forward direction.

In one example, the algorithm performs a single and double integration of the acceleration signal 602 during the integration time between the beginning of the stride and the end of the stride. The single integration of the acceleration signal results in the speed v(t) of the travelling foot as a function of time, while the double integral of the acceleration signal gives the travelled distance x(t) of the foot as a function of time.

As shown in FIG. 6, the period of a complete footstep of the runner (i.e., a step time 616) may be measured between the identified foot-strike events of the runner. The portion of each measured step time 616 during which the user's foot is in contact with the running surface (i.e., a foot on ground time 620) may be measured between each detected foot-strike event and a subsequently-detected toe-off event 704.

The portion of each measured step time 616 during which the user's foot is airborne (i.e., a foot in air time 618) may be measured between each detected toe-off event and a subsequently-detected foot-strike event. Thus, for each complete footstep taken by the user, an accurate measurement may be made of each step time 616 of the user, as well as the portions of that step time 616 attributable to foot on ground time 620 and foot in air time 618. A complete footstep means a movement cycle during which the foot of a user begins in a particular position and again returns to that same position. In one example, this information may be used by processors at the sensor unit 2 or sensor unit 4 to accurately calculate the speed and/or pace of the user, the distance traveled by the user, etc., during the corresponding footstep taken by the user.

In one example, radio transmissions between the foot-mounted sensor unit 4 and the wrist-mounted sensor unit 2 may be made only during the time during which the foot is on the ground because the controller 44 need not be employed to monitor the signal 602 during these time periods. After each foot-strike event the foot of the user will necessarily be on the ground for at least a minimum period of time, and it is not necessary during this period of time to analyze the signal 602 to identify potential occurrences of a toe-off event. Therefore, it is possible to ignore the signals during this particular period of time. Similarly, in one example, calculations involving data accumulated by the foot-mounted sensor unit 4 may be made only during this foot on the ground time 620, thereby consuming processing power only during time periods when the signal 602 need not be actively analyzed.

Similar to the manner in which the accelerometer output signal of a foot mounted accelerometer within sensor unit 4 is processed, the accelerometer output signal of an arm mounted accelerometer within sensor unit 2 is processed. However, analysis of the arm acceleration signal is simplified in that the signal does not contain characteristics associated with a ground strike nor a period of time in which the arm remains on the ground. Rather, during running, the user arm is typically swung forward and backward in a periodic manner. Sensor unit 2 and sensor unit 4 are synchronized in time and clocking to compare the outputs of sensor unit 2 and sensor unit 4.

The arm acceleration signal may fluctuate dynamically in response to movement of the user's arm that occur when the user is walking or running. In one example, the accelerometer is oriented such that when the level of the arm mounted accelerometer signal is greater than zero, this indicates that the accelerometer is sensing a positive acceleration along the acceleration sensing axis, and when the level of the arm mounted accelerometer signal is less than zero, this indicates that the accelerometer is sensing a negative acceleration along the acceleration axis. The accelerometer output signal may be converted into digital values, in which case the positive/negative acceleration boundary may be an arbitrary positive value instead of zero.

The arm acceleration signal is subjected to an algorithm executed by a microprocessor. In one example, a smoothed version of the arm acceleration signal is constantly monitored to simplify monitoring. For example, a smoothed signal resembling a sinusoidal signal representing back and forth motion of the arm in a direction of sensitivity may be monitored.

Particular characteristics of the arm acceleration signal may be identified which are indicative of particular occurrences during each arm swing. In one example, the arm acceleration signal is analyzed utilizing an algorithm to (1) identify occasions when the user's arm is being swung forward in the direction of locomotion, and (2) to identify occasions when the user's arm is being swung backward in a direction opposite the direction of locomotion, and (3) to identify occasions and/or the extent to which the user's arm is being swung rotationally about the user's torso.

In one example, forward swings/movement of the arm are identified by monitoring the arm acceleration signal for characteristics that indicate the arm is being swung forward. In one example, the acceleration signal is analyzed to identify periods of negative acceleration. In one example, an increasing negative acceleration leading to a large negative peak is identified.

In one example, rearward swings/movement of the arm are identified by monitoring the arm acceleration signal for characteristics that indicate the arm is being swung rearward. In one example, the acceleration signal is analyzed to identify periods of positive acceleration. In one example, an increasing positive acceleration leading to a large positive peak is identified. In further examples, other algorithms may be utilized to determine the direction which the user arm is being swung. Although the user arm swing may have both a forward/reverse component and an up/down component, in one example, only sensitivity in the forward/reverse direction is analyzed. In further examples, sensitivity in the up/down direction is analyzed and/or sensitivity in a rotational direction about the user torso or left/right direction across the user body is analyzed in addition to the forward/reverse direction.

The system can be further extended by including in sensor unit 2 additional accelerometers oriented to measure arm swing in different directions. In a further example, three perpendicularly oriented linear accelerometers or a triaxial accelerometer sensitive to movement in three perpendicular directions is utilized to monitor the user arm swing in a plurality of directions, including forward/reverse (e.g., relative to the direction of locomotion), left/right (e.g., across the user's torso/body towards the opposite arm), and up/down (along an axis defined by and running through the user's head and feet). In one example, the user arm swing in a left/right direction and up/down direction is determined in much the same way as the forward/reverse swing is measured. In a further example, rotation of the arm about the user torso can be measured using a gyroscope.

In one example, a forward/reverse to left/right ratio is calculated. For example, where the sensor unit 2 is worn on the left arm, the amount of displacement (or alternatively, acceleration) in the forward direction is compared to the amount of the displacement (or alternatively, acceleration) in the rightward direction.

In a further example, a forward/reverse to up/down ratio is calculated. In a further example, a forward/reverse to rotation ratio is calculated. For any direction, either the displacement or acceleration may be measured.

In one example, too much left to right motion of the left arm or right to left motion of the right arm indicates the user is undesirably rotating the torso rather than maintaining it in a forward direction. Too much left to right motion of the left arm or right to left motion of the right arm may also indicate undesirable running form even when the user torso is not rotating back and forth during locomotion. Movement of the user torso is independently measured using chest mounted sensors as described herein. In one example, the system detects whether the user is undesirably swinging his arms in a left to right manner while maintaining a relatively still torso. In one example, the system detects whether the user is both undesirably swinging his arms in a left to right manner and undesirably rotating his torso during locomotion. In one example, the system detects whether the user is undesirably rotating the user torso even if the arms are maintained in a desired forward/reverse direction.

In further examples, the user may wear sensor unit 2 on his right arm instead of his left, or the user may wear sensor units having the necessary functionality of sensor unit 2 on both the left and right arm to monitor both arms and determine whether arm motion is symmetrical for both the left arm and the right arm.

As described previously, a learning/calibration mode (also referred to as a test mode herein) may be utilized to set the threshold values for the amount of rotation of the torso or left/right movement of the arms below which is acceptable and above which is unacceptable. As described previously, during learning mode where the runner is instructed to run with the desired form, and various parameters are measured corresponding to the desired range of motion. Often, the runner may be able to run with correct form for a brief time, as in the test mode, but will deviate if not completely mindful of correct form, as during longer training runs or races where the runner is otherwise occupied. These values are then stored and then used to compare to the actual motion of the runner during running. If the runner deviates from the test established values, an alarm is output. The learning/calibration mode may be utilized to establish threshold values for any monitored parameter, including opposite arm/leg synchronization, torso vertical displacement during locomotion, torso rotation, torso horizontal movement, arm horizontal movement (e.g., left to right or right to left), arm rotation (e.g., arm twisting) about the torso.

In the learning mode where the runner consciously minimized movement, the system stores measurements for how much side to side/rotational twisting occurred, and up/down movement occurred. Alternatively, values can be set at the factory based on tests of other normal users or based on elite athletes performing at a high level. Also, the settings may be varied based on a current speed of user. The system allows individual coaches and users option of modifying settings based on their ability levels, natural running style, current running form (e.g., adjust settings as user improves form), etc.

During running, it is desirable for the user to minimize unnecessary movement of the torso, either up and down, side to side, or rotational/twisting. In one example, the chest strap includes a rotation sensor to determine torso rotation. Rotation about an axis running the length of the user torso is measured (e.g., the left shoulder moves forward in the direction of travel while the right shoulder simultaneously moves rearward). In one example, the rotation sensor is a pair of spaced substantially parallel accelerometer sensors 50a and 50b which can be used to calculate angular acceleration based on the difference of the signals. In another embodiment, the rotation sensor is a gyroscope.

In one example, sensors 50a and 50b are triaxial accelerometers, thereby enabling measurement of the user torso in a multitude of directions. For example, the two accelerometers are utilized to measure horizontal (e.g., side to side or left to right) movement of the torso along an axis running perpendicular to the vertical length of the torso.

In one example, the chest strap includes at least one accelerometer oriented to measure acceleration along an axis perpendicular to the running surface (i.e., in a direction running the length of the user torso). This accelerometer may be utilized to calculate the height/distance that the torso moves along this axis during location in a manner similar to that described above in calculating distance travelled of a foot stride in the direction of locomotion. Utilizing a chest mounted accelerometer to calculate the distance the runner travels in the vertical direction (i.e., the vertical displacement height during the striding motion) is preferable over utilizing foot mounted sensors to perform this calculation as calculations are simplified since the motion of the torso during striding is less complex than the user foot which, for example, travels rearward and upward to a height not representative of the overall vertical displacement height.

In a further example, the chest strap includes at least two accelerometers in a substantially mutually perpendicular orientation which provide signals for use by the processing system to determine acceleration both along an axis perpendicular to the running surface and along an axis parallel to the running surface running from the back of the user torso to the front of the user torso in the direction of locomotion. These two accelerometers may be utilized to calculate a striding angle of the torso in the forward and upward direction.

In a further example, in addition to the two accelerometers mounted in a substantially mutually perpendicular orientation as discussed above, a third accelerometer is included. The third accelerometer is mounted in a direction substantially perpendicular to the other two accelerometers. The acceleration measured by the third accelerometer is used to determine the amount of motion along an axis running from the left side of the user body to the right side of the user body (i.e., side to side or left to right). In general, excess motion in this direction during running is undesirable. In one example, a triaxial accelerometer may be used in place of the one, two, or three accelerometer embodiments to measure acceleration in any of the desired directions of motion.

In one example, sensors 50a and 50b are two tri-axial accelerometers placed in parallel within the chest strap on each side of the user torso. The output of the two tri-axial accelerometers is processed to measure vertical displacement height during locomotion, torso rotation, left to right motion, or other undesirable torso motion.

Figure 7:
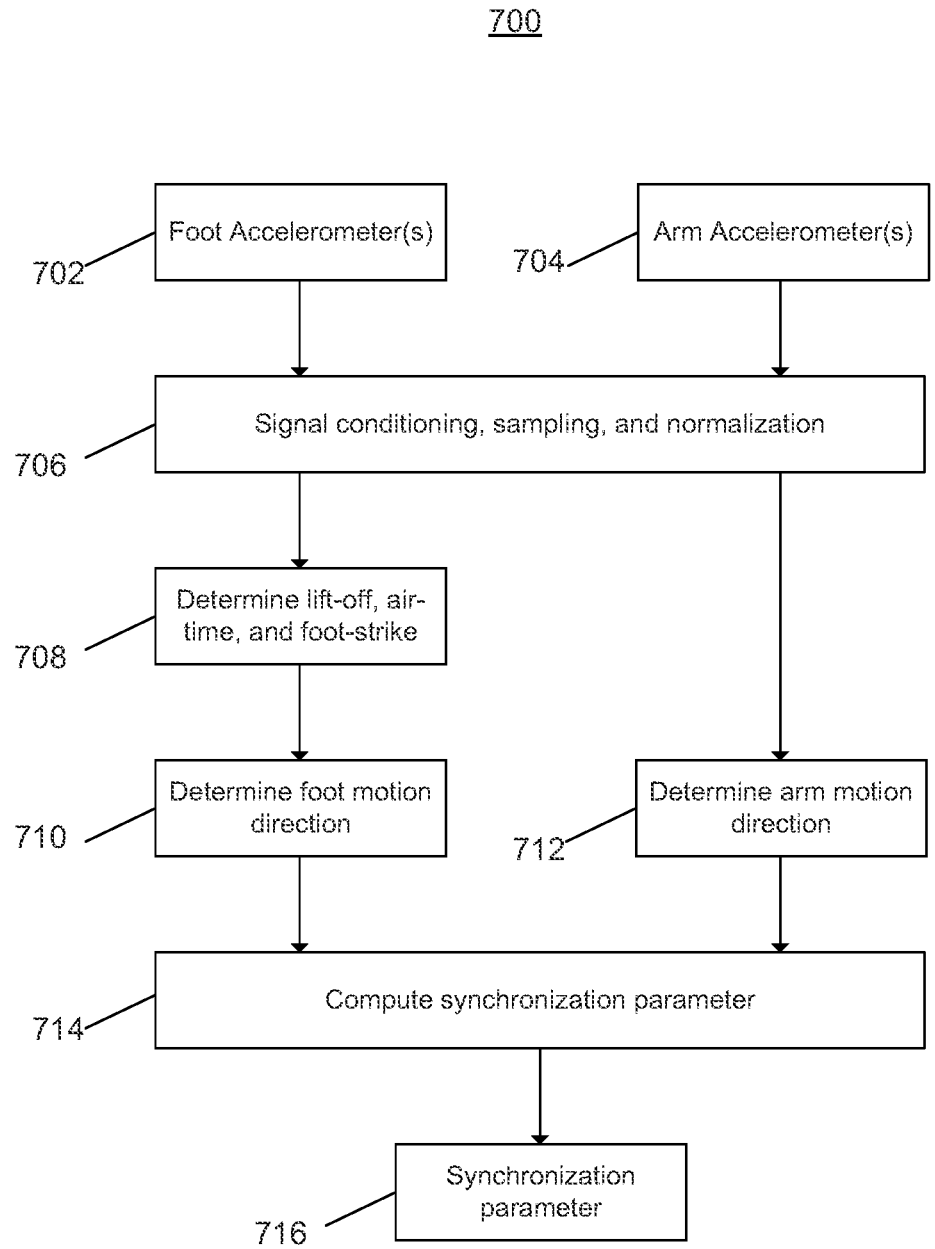
FIG. 7 illustrates an exemplary processing method.

FIG. 7 illustrates an exemplary processing method 700. Acceleration signals for each accelerometer 702, 704 in the system are sampled and stored for the duration of each user stride and processed as detailed in the exemplary block diagram of FIG. 7.

At block 706, the acceleration signals output from the foot mounted accelerometers are conditioned, sampled, and normalized. Similarly, the acceleration signals output from the arm mounted accelerometers are conditioned, sampled, and normalized.

At block 708, the acceleration signals output from the foot mounted accelerometers 702 are analyzed to determine lift off (e.g., toe-off), air-time, and foot-strike for each stride. At block 710, a foot direction motion is determined. At block 712, the acceleration signals output from the arm mounted accelerometers 704 are analyzed to determine an arm direction motion for each stride.

At block 714, utilizing the foot and arm direction motion, a synchronization parameter 716 is computed and output. For example, the amount of time in which the user foot and arm are moving in a same direction may be calculated. In one example, the calculated synchronization parameter is compared to a threshold value determined via a learning mode. In a further example, the calculated synchronized parameter is compared to a pre-determined value stored during manufacturing of the system.

Figure 8:
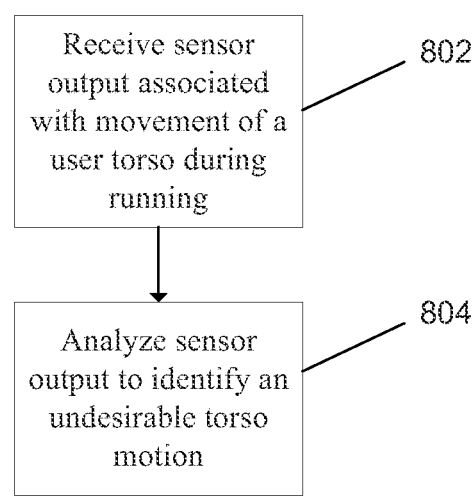
FIG. 8 is a flow diagram illustrating a method for monitoring a user stride in one example.

FIG. 8 is a flow diagram illustrating a method for monitoring a user stride in one example. At block 802, a sensor output associated with movement of a user torso during running is received. At block 804, the sensor output is analyzed to identify an undesirable torso motion. In one example, the undesirable torso motion is a torso stride angle, a torso vertical displacement, a torso vertical acceleration, or a torso rotation in excess of a threshold value. In one example, the method further includes receiving a user speed data. The threshold value may be dependent on a user speed.

Figure 9:
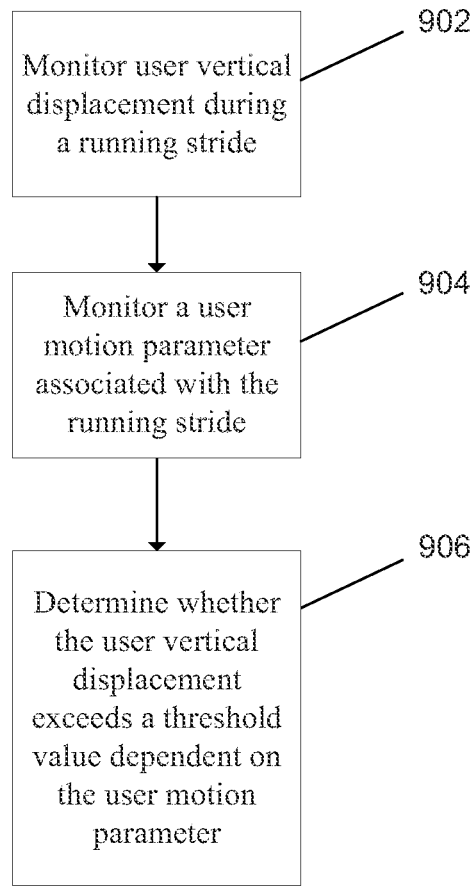
FIG. 9 is a flow diagram illustrating a method for monitoring a user stride in a further example.

FIG. 9 is a flow diagram illustrating a method for monitoring a user stride in a further example. At block 902, a user vertical displacement during a running stride is monitored. At block 904, a user motion parameter associated with the running stride is monitored. For example, the user motion parameter is a user horizontal displacement during the running stride or a user speed during the running stride. At block 906, it is determined whether the user vertical displacement exceeds a threshold value, where the threshold value is dependent on the user motion parameter.

While the exemplary embodiments of the present invention are described and illustrated herein, it will be appreciated that they are merely illustrative and that modifications can be made to these embodiments without departing from the spirit and scope of the invention. For example, although examples are described with respect to running activities, methods and apparatuses described herein may be used for other athletic activities in further examples. Thus, the scope of the invention is intended to be defined only in terms of the following claims as may be amended, with each claim being expressly incorporated into this Description of Specific Embodiments as an embodiment of the invention.

What is claimed is:

1. A wrist-worn device comprising:
   a gyroscope to output gyroscope outputs;
   a global positioning system unit to output global positioning system unit outputs;
   a transceiver to output transceiver signals;
   one or more accelerometers to output accelerometer signals;
   one or more computer memories;

one or more processors operably connected to the gyroscope, the global positioning system unit, the transceiver, the one or more accelerometers, and the one or more computer memories, wherein the one or more processors are configured to:

obtain a user data from the gyroscope outputs, global positioning system unit outputs, the accelerometer signals and the transceiver signals, wherein the user data comprises a vertical displacement, a stride length, an arm motion, and a speed;

identify an undesirable motion from the user data; and one or more user interfaces operably connected to the one or more processors and configured to adjust user interface outputs, over time, comprising the vertical displacement, the stride length, and the speed, wherein the one or more user interfaces are further configured to output an indication of the undesirable motion.

2. The wrist-worn device of claim 1, wherein the undesirable motion comprises a motion in excess of a threshold value.

3. The wrist-worn device of claim 1, wherein the one or more processors are further configured to determine a user impact based on the user data.

4. The wrist-worn device of claim 1, wherein the user data comprises a motion data over a period of time, and wherein determining the undesirable motion comprises determining, based on the motion data, a motion of a user wrist obtained from at least one selected from outputs obtained from the gyroscope and outputs obtained from the one or more accelerometers.

5. The wrist-worn device of claim 4, wherein the motion data comprises:

a first signal indicating an acceleration measured by the one or more accelerometers over time; and a second signal indicating a rotation measured by the gyroscope over time.

6. The wrist-worn device of claim 1, wherein the user data comprises a motion data over a period of time during a user motion comprising at least one selected from a walking motion and a running motion, and the one or more processors are further configured to:

determine a user speed based on the user data;

determine a plurality of user impacts over time based on the user data; and determine a user altitude based on the user data, wherein the wrist-worn device further comprises an altimeter.

7. The wrist-worn device of claim 1, wherein the one or more processors are configured to:

determine a user impact based on the user data;

determine one or more of characteristics of a user; and determine based on the user data and the one or more characteristics of the user the undesirable motion has occurred.

8. The wrist-worn device of claim 7, wherein the one or more characteristics of the user are identified from a historical user physical activity.

9. The wrist-worn device of claim 7, wherein the one or more characteristics of the user comprise a historical measured user motion of the user.

10. The wrist-worn device of claim 9, wherein the undesirable motion is identified from the historical measured user motion of the user.

11. The wrist-worn device of claim 7, wherein the undesirable motion is identified by a user parameter in excess of a threshold value, and the one or more user interfaces further configured to output the indication of the undesirable motion responsive to identifying the user parameter in excess of the threshold value.

12. The wrist-worn device of claim 11, wherein the threshold value is derived from the one or more characteristics of the user.

13. The wrist-worn device of claim 11, wherein the threshold value is associated with a user speed.

14. The wrist-worn device of claim 11, wherein the threshold value is derived from empirically collected sample data.

15. The wrist-worn device of claim 7, wherein the user data comprises sensor outputs received at the transceiver from one or more sensors remote from the wrist-worn device.

16. The wrist-worn device of claim 1, wherein the one or more processors are configured to:

obtain from the one or more computer memories a recorded data, the recorded data comprising: an indication of a user motion previously experienced by a user of the wrist-worn device, the indication of the user motion obtained from sensor data generated by one or more first sensors worn by the user during the user motion previously experienced by the user, the one or more first sensors comprising the one or more accelerometers at the wrist-worn device;

obtain, by the wrist-worn device, additional sensor data generated by one or more second sensors worn by the user over a period of time, the one or more second sensors comprising the one or more accelerometers at the wrist-worn device, and wherein the user data comprises the additional sensor data generated by the one or more second sensors;

identify the undesirable motion from the user data, by the wrist-worn device, during the period of time based on the recorded data and the additional sensor data; and generate, by the wrist-worn device, a notification based on the undesirable motion identified during the period of time, the notification comprising the indication of the undesirable motion.

17. The wrist-worn device of claim 16, wherein the one or more first sensors and the one or more second sensors comprise at least one of the gyroscope or an accelerometer selected from the one or more accelerometers, the gyroscope outputs indicating an orientation measured by the gyroscope during the period of time.

18. The wrist-worn device of claim 16, wherein the one or more first sensors comprise the gyroscope and at least one of the one or more accelerometers, and the one or more second sensors comprise the gyroscope and at least one of the one or more accelerometers, the gyroscope outputs indicating an orientation measured by the gyroscope during the period of time.

19. The wrist-worn device of claim 16, wherein the additional sensor data generated by the one or more second sensors comprise a measured acceleration in an inertial z-direction perpendicular to the ground.

20. The wrist-worn device of claim 17, wherein the undesirable motion is identified based in part on identifying an accelerometer output signal exceeds a threshold value.

21. The wrist-worn device of claim 1, wherein the one or more processors are configured to:

obtain, by the wrist-worn device, sample data generated a plurality of sensors over a time period, wherein the plurality of sensors is worn by a user, and wherein the sample data comprises the user data, wherein the user data further comprises a heart rate data indicating a heart rate of the user obtained from one or more heart rate sensors of the plurality of sensors.

22. The wrist-worn device of claim 1, wherein the undesirable motion identified from the user data comprises an undesirable body motion identified at least from the accelerometer signals output from the one or more accelerometers at the wrist-worn device, the undesirable body motion comprising an undesired torso motion.

23. The wrist-worn device of claim 1, wherein the user data is obtained during a user running motion and comprises the accelerometer signals responsive to a user arm motion during the user running motion.

24. The wrist-worn device of claim 23, wherein the undesirable motion is identified if an arm acceleration obtained from the accelerometer signals exceed a threshold value.

25. The wrist-worn device of claim 24, wherein the threshold value is determined from empirically collected sample data.

26. The wrist-worn device of claim 1, wherein the user data is obtained during a user walking motion and comprises accelerometer signals output from the one or more accelerometers responsive to a user arm motion during the user walking motion, and the undesirable motion is identified during the user walking motion, wherein the undesirable motion comprises an undesirable user torso motion identified from the user arm motion by identifying an arm acceleration obtained from the accelerometer signals exceeds a threshold value, the threshold value determined from empirically collected sample data.

27. The wrist-worn device of claim 1, wherein the undesirable motion identified from the user data comprises an undesirable body motion identified at least from the accelerometer signals output from the one or more accelerometers at the wrist-worn device and the gyroscope outputs, the undesirable body motion comprising an undesirable torso motion, wherein the user data is obtained during a user running motion and comprise the accelerometer signals responsive to a user arm motion during the user running motion and the gyroscope outputs responsive to the user arm motion during the user running motion, wherein the undesirable torso motion is identified if an arm acceleration obtained from the accelerometer signals exceed a first threshold value and an arm orientation obtained from the gyroscope outputs exceeds a second threshold value, wherein the first threshold value and the second threshold value are determined from empirically collected sample data.

28. A wrist-worn device comprising:
a gyroscope to output gyroscope outputs;
a global positioning system unit to output global positioning system unit outputs;
a transceiver to output transceiver signals;
one or more accelerometers to output accelerometer signals;
one or more computer memories;
one or more processors operably connected to the gyroscope, the global positioning system unit, the transceiver, the one or more accelerometers, and the one or more computer memories, wherein the one or more processors are configured to:
obtain a user data from the gyroscope outputs, global positioning system unit outputs, the accelerometer signals and the transceiver signals, wherein the user data comprises a vertical displacement, a stride length, an arm motion, and a speed, wherein the user data comprises a motion data over a period of time, wherein the user data is obtained during a user walking motion;
identify an undesirable motion from the user data, wherein the undesirable motion is identified, based on the motion data, a motion of a user wrist obtained from at least one selected from outputs obtained from the gyroscope and outputs obtained from the one or more accelerometers;
determine a user speed from the global positioning system unit outputs;
determine a user altitude based on altimeter outputs, wherein the wrist-worn device further comprises an altimeter to output the altimeter outputs;
determine a user impact based on the user data;
determine one or more characteristics of a user;
determine based on the user data and the one or more characteristics of the user the undesirable motion has occurred, wherein the undesirable motion is identified by a user parameter in excess of a threshold value, wherein the threshold value is derived from the one or more characteristics of the user or empirically collected sample data; and
one or more user interfaces operably connected to the one or more processors and configured to adjust user interface outputs, over time, comprising the vertical displacement, the stride length, and the speed, wherein the one or more user interfaces are further configured to output an indication of the undesirable motion responsive to identifying the user parameter in excess of the threshold value.

29. A wrist-worn device comprising:
a gyroscope to output gyroscope outputs;
a global positioning system unit to output global positioning system unit outputs;
a transceiver to output transceiver signals;
one or more accelerometers to output accelerometer signals;
one or more computer memories;
one or more processors operably connected to the gyroscope, the global positioning system unit, the transceiver, the one or more accelerometers, and the one or more computer memories, wherein the one or more processors are configured to:
obtain a user data from the gyroscope outputs, global positioning system unit outputs, the accelerometer signals and the transceiver signals, wherein the user data comprises a vertical displacement, a stride length, an arm motion, and a speed, wherein the user data comprises a motion data over a period of time, wherein the user data is obtained during one selected from a user walking motion and a user running motion;
identify an undesirable motion from the user data, wherein the undesirable motion is identified, based on the motion data, a motion of a user wrist obtained from at least one selected from outputs obtained from the gyroscope and outputs obtained from the one or more accelerometers;
determine a user speed from the global positioning system unit outputs;
determine a user altitude based on altimeter outputs, wherein the wrist-worn device further comprises an altimeter to output the altimeter outputs;
determine a user impact based on the user data;
determine one or more characteristics of a user;

determine based on the user data and the one or more characteristics of the user the undesirable motion has occurred, wherein the undesirable motion is identified by a user parameter in excess of a threshold value, wherein the threshold value is derived from the one or more characteristics of the user or empirically collected sample data;

one or more user interfaces operably connected to the one or more processors and configured to adjust user interface outputs, over time, comprising the vertical displacement, the stride length, and the speed, wherein the one or more user interfaces are further configured to output an indication of the undesirable motion responsive to identifying the user parameter in excess of the threshold value, wherein the one or more processors are configured to:
obtain from the one or more computer memories a recorded data, the recorded data comprising: an indication of a user motion previously experienced by a user of the wrist-worn device, the indication of the user motion obtained from sensor data generated by one or more first sensors worn by the user during the user motion previously experienced by the user, the one or more first sensors comprising the one or more accelerometers at the wrist-worn device;

obtain, by the wrist-worn device, additional sensor data generated by one or more second sensors worn by the user over a period of time, the one or more second sensors comprising the one or more accelerometers at the wrist-worn device, and wherein the user data comprises the additional sensor data generated by the one or more second sensors;

identify the undesirable motion from the user data, by the wrist-worn device, during the period of time based on the recorded data and the additional sensor data; and generate, by the wrist-worn device, a notification based on the undesirable motion identified during the period of time, the notification comprising the indication of the undesirable motion.

* * * * *